United States Patent
Kalinski

(10) Patent No.: US 12,059,434 B2
(45) Date of Patent: Aug. 13, 2024

(54) SHORT-TERM ACTIVATED DC1S AND METHODS FOR THEIR PRODUCTION AND USE

(71) Applicant: UNIVERSITY OF PITTSBURGH-OF THE COMMONWEALTH SYSTEM OF HIGHER EDUCATION, Pittsburgh, PA (US)

(72) Inventor: Pawel Kalinski, East Aurora, NY (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 152 days.

(21) Appl. No.: 16/488,702

(22) PCT Filed: Feb. 28, 2018

(86) PCT No.: PCT/US2018/020179
§ 371 (c)(1),
(2) Date: Aug. 26, 2019

(87) PCT Pub. No.: WO2018/160666
PCT Pub. Date: Sep. 7, 2018

(65) Prior Publication Data
US 2020/0038440 A1 Feb. 6, 2020

Related U.S. Application Data

(60) Provisional application No. 62/464,671, filed on Feb. 28, 2017.

(51) Int. Cl.
*A61K 35/15* (2015.01)
*C12N 5/0784* (2010.01)

(52) U.S. Cl.
CPC ............ *A61K 35/15* (2013.01); *C12N 5/0639* (2013.01); *C12N 2501/24* (2013.01)

(58) Field of Classification Search
None
See application file for complete search history.

(56) References Cited

U.S. PATENT DOCUMENTS

| | | | |
|---|---|---|---|
| 2005/0003533 A1* | 1/2005 | Kalinski | C12N 5/064 435/372 |
| 2005/0059151 A1 | 3/2005 | Bosch | |
| 2006/0057120 A1 | 3/2006 | Bosch | |
| 2012/0251561 A1 | 10/2012 | Bosch | |
| 2013/0183343 A1 | 7/2013 | Czerniecki et al. | |
| 2014/0220675 A1 | 8/2014 | Kalinski | |

FOREIGN PATENT DOCUMENTS

| | | |
|---|---|---|
| WO | 2004053072 | 6/2004 |
| WO | 2017004230 | 1/2017 |

OTHER PUBLICATIONS

Felzmann et al., 2005, Can. Immunol. Immunother. vol. 54: 769-780.*
Lagenkamp et al., 2000, Nat. Immunol. vol. 1: 311-316.*
Yamada, Noriyuki, et al. "CD8+ tumor-infiltrating lymphocytes predict favorable prognosis in malignant pleural mesothelioma after resection." Cancer immunology, immunotherapy 59.10 (2010): 1543-1549.
Anraku, Masaki, et al. "Impact of tumor-infiltrating T cells on survival in patients with malignant pleural mesothelioma." The Journal of thoracic and cardiovascular surgery 135.4 (2008): 823-829.
Galon, Jérôme, et al. "Type, density, and location of immune cells within human colorectal tumors predict clinical outcome." Science 313.5795 (2006): 1960-1964.
Clarke, Sarah L., et al. "CD4+ CD25+ FOXP3+ regulatory T cells suppress anti-tumor immune responses in patients with colorectal cancer." PloS one 1.1 (2006): e129.
Michel, S., et al. "High density of FOXP3-positive T cells infiltrating colorectal cancers with microsatellite instability." British journal of cancer 99.11 (2008): 1867-1873.
Curiel, Tyler J., et al. "Specific recruitment of regulatory T cells in ovarian carcinoma fosters immune privilege and predicts reduced survival." Nature medicine 10.9 (2004): 942.
Tumeh, Paul C., et al. "PD-1 blockade induces responses by inhibiting adaptive immune resistance." Nature 515.7528 (2014): 568.
Herbst, Roy S., et al. "Predictive correlates of response to the anti-PD-L1 antibody MPDL3280A in cancer patients." Nature 515.7528 (2014): 563.
Topalian, Suzanne L., et al. "Safety, activity, and immune correlates of anti-PD-1 antibody in cancer." New England Journal of Medicine 366.26 (2012): 2443-2454.
Bonecchi, Raffaella, et al. "Differential expression of chemokine receptors and chemotactic responsiveness of type 1 T helper cells (Th1s) and Th2s." Journal of Experimental Medicine 187.1 (1998): 129-134.
Hirai, Hiroyuki, et al. "Prostaglandin D2 selectively induces chemotaxis in T helper type 2 cells, eosinophils, and basophils via seven-transmembrane receptor CRTH2." Journal of Experimental Medicine 193.2 (2001): 255-262.
Musha, Hiroaki, et al. "Selective infiltration of CCR5+ CXCR3+ T lymphocytes in human colorectal carcinoma." International journal of cancer 116.6 (2005): 949-956.
Kunz, M., et al. "Strong expression of the lymphoattractant C-X-C chemokine Mig is associated with heavy infiltration of T cells in human malignant melanoma." The Journal of pathology 189.4 (1999): 552-558.
Ohtani, H., et al. "Abundant expression of CXCL9 (MIG) by stromal cells that include dendritic cells and accumulation of CXCR3+ T cells in lymphocyte-rich gastric carcinoma." The Journal of Pathology: A Journal of the Pathological Society of Great Britain and Ireland 217.1 (2009): 21-31.

(Continued)

*Primary Examiner* — Amy E Juedes
(74) *Attorney, Agent, or Firm* — Meunier Carlin & Curfman LLC

(57) ABSTRACT

Provided herein are ST-αDC1 and populations of those cells, methods for making ST-αDC1 and populations of those cells, and methods for using ST-αDC1 and populations of those cells for the treatment of cancer, precancerous conditions and chronic infections.

5 Claims, 8 Drawing Sheets

(56) References Cited

OTHER PUBLICATIONS

Soumaoro, Labile Togba, et al. "Cyclooxygenase-2 expression: a significant prognostic indicator for patients with colorectal cancer." Clinical Cancer Research 10.24 (2004): 8465-8471.

Williams, et al., "The Role of COX-2 in Intestinal Cancer" Ann. NY Acad. Sci. (1999) 889:72-83.

Obermajer, Nataša, et al. "PGE2-induced CXCL12 production and CXCR4 expression controls the accumulation of human MDSCs in ovarian cancer environment." Cancer research 71.24 (2011): 7463-7470.

Muthuswamy, et al., "NF-KB Hyperactivation in Tumor Tissues Allows TumorSelective Reprogramming of the Chemokine Microenvironment to Enhance the Recruitment of Cytolytic T Effector Cells" Cancer Res., (2012) 72:3735-3743.

Giermasz, Adam S., et al. "Type-1 polarized dendritic cells primed for high IL-12 production show enhanced activity as cancer vaccines." Cancer immunology, immunotherapy 58.8 (2009): 1329-1336.

Lee, Je-Jung, et al. "Type 1-polarized dendritic cells loaded with autologous tumor are a potent immunogen against chronic lymphocytic leukemia." Journal of leukocyte biology 84.1 (2008): 319-325.

Wieckowski, Eva, et al. "Type-1 polarized dendritic cells loaded with apoptotic prostate cancer cells are potent inducers of CD8+ T cells against prostate cancer cells and defined prostate cancer-specific epitopes." The Prostate 71.2 (2011): 125-133.

Okada, Hideho, et al. "Induction of CD8+ T-cell responses against novel glioma-associated antigen peptides and clinical activity by vaccinations with α-type 1 polarized dendritic cells and polyinosinic-polycytidylic acid stabilized by lysine and carboxymethylcellulose in patients with recurrent malignant glioma." Journal of Clinical Oncology 29.3 (2011): 330.

Budiu, R. A., et al. "Immunobiology of human mucin 1 in a preclinical ovarian tumor model." Oncogene 32.32 (2013): 3664.

Vieira, Pedro L., et al. "Development of Th1-inducing capacity in myeloid dendritic cells requires environmental instruction." The Journal of Immunology 164.9 (2000): 4507-4512.

Mailliard, Robbie B., et al. "α-type-1 polarized dendritic cells: a novel immunization tool with optimized CTL-inducing activity." Cancer research 64.17 (2004): 5934-5937.

Watchmaker, Payal B., et al. "Independent regulation of chemokine responsiveness and cytolytic function versus CD8+ T cell expansion by dendritic cells." The journal of immunology 184.2 (2010): 591-597.

Wesa, Amy, et al. "Polarized type-1 dendritic cells (DC1) producing high levels of IL-12 family members rescue patient TH1-type antimelanoma CD4+ T cell responses in vitro." Journal of immunotherapy 30.1 (2007): 75-82.

Langenkamp, Anja, et al. "Kinetics of dendritic cell activation: impact on priming of T H 1, T H 2 and nonpolarized T cells." Nature immunology 1.4 (2000): 311.

Muthuswamy, Ravikumar, et al. "Ability of mature dendritic cells to interact with regulatory T cells is imprinted during maturation." Cancer research 68.14 (2008): 5972-5978.

Gustafsson, Karin, et al. "Recruitment and activation of natural killer cells in vitro by a human dendritic cell vaccine." Cancer research 68.14 (2008): 5965-5971.

Pagès, Franck, et al. "Effector memory T cells, early metastasis, and survival in colorectal cancer." New England journal of medicine 353.25 (2005): 2654-2666.

Chaput, Nathalie, et al. "Identification of CD8+ CD25+ Foxp3+ suppressive T cells in colorectal cancer tissue." Gut 58.4 (2009): 520-529.

Rosenberg, Steven A., James C. Yang, and Nicholas P. Restifo. "Cancer immunotherapy: moving beyond current vaccines." Nature medicine 10.9 (2004): 909.

Palucka, Karolina, and Jacques Banchereau. "How dendritic cells and microbes interact to elicit or subvert protective immune responses." Current opinion in immunology 14.4 (2002): 420-431.

Banchereau, Jacques, and Ralph M. Steinman. "Dendritic cells and the control of immunity." Nature 392.6673 (1998): 245.

Enk, Alexander H., et al. "Dendritic cells as mediators of tumor-induced tolerance in metastatic melanoma." International journal of cancer 73.3 (1997): 309-316.

Muthuswamy, Ravikumar, et al. "PGE2 transiently enhances DC expression of CCR7 but inhibits the ability of DCs to produce CCL19 and attract naive T cells." Blood 116.9 (2010): 1454-1459.

López-Albaitero, Andrés, et al. "Maturation pathways of dendritic cells determine TAP1 and TAP2 levels and cross-presenting function." Journal of immunotherapy (Hagerstown, Md.: 1997) 32.5 (2009): 465.

Brahmer, Julie R., et al. "Safety and activity of anti-PD-L1 antibody in patients with advanced cancer." New England Journal of Medicine 366.26 (2012): 2455-2465.

Taube, Janis M., et al. "Association of PD-1, PD-1 ligands, and other features of the tumor immune microenvironment with response to anti-PD-1 therapy." Clinical cancer research 20.19 (2014): 5064-5074.

Gatalica, Zoran, et al. "Programmed cell death 1 (PD-1) and its ligand (PD-L1) in common cancers and their correlation with molecular cancer type." Cancer Epidemiology and Prevention Biomarkers 23.12 (2014): 2965-2970.

Llosa, Nicolas J., et al. "The vigorous immune microenvironment of microsatellite instable colon cancer is balanced by multiple counter-inhibitory checkpoints." Cancer discovery 5.1 (2015): 43-51.

Kroemer, Guido, et al. "Colorectal cancer: the first neoplasia found to be under immunosurveillance and the last one to respond to immunotherapy?. " Oncoimmunology 4.7 (2015): e1058597.

International Search Report and Written Opinion dated May 25, 2018, from International Application No. PCT/US2018/020179, 9 pages.

Okada, H. et al. "Induction of CD8+ T-Cell Responses Against Novel Glioma-Associated Antigen Peptides and Clinical Activity by Vaccinations With a-Type 1 Polarized Dendritic Cells and Polyinosinic-Polycytidylic Acid Stabilized by Lysine and Carboxymethylcellulose in Patients With Recurrent Malignant Glioma", Journal of Clinical Oncology, vol. 29, No. 3, 2011.

Akiyama, Y. et al. "α-type-1 polarized dendritic cell-based vaccination in recurrent high-grade glioma: a phase I clinical trial", BMC Cancer 2012, 12:623.

Mailliard, R. et al. "a-Type-1 Polarized Dendritic Cells: A Novel Immunization Tool with Optimized CTL-inducing Activity", Cancer Research 64, 5934-5937, 2004.

Langenkamp, A. et al. "Kinetics of dendritic cell activation: impact on priming of TH1, TH2 and nonpolarized T cells", Nature Immunology, vol. 1, No. 4, Oct. 2000.

Kalinski, P. et al. "Final Maturation of Dendritic Cells Is Associated with Impaired Responsiveness to IFN-y and to Bacterial IL-12 Inducers: Decreased Ability of Mature Dendritic Cells to Produce IL-12 During the Interaction with Th Cells", The Journal of Immunology; 162:3231-3236, 1999.

Kalinski, P. et al. "T-cell priming by type-1and type-2 polarized dendritic cells: the concept of a third signal", Viewpoint Immunology Today, vol. 20, No. 12, Dec. 1999.

Della Bella et al.; "Functional repertoire of dendritic cells generated in granulocyte macrophage-colony stimulating factor and interferon-alpha" Journal of Leukocyte Biology, vol. 75; dated Jan. 2004; 12 pages.

\* cited by examiner

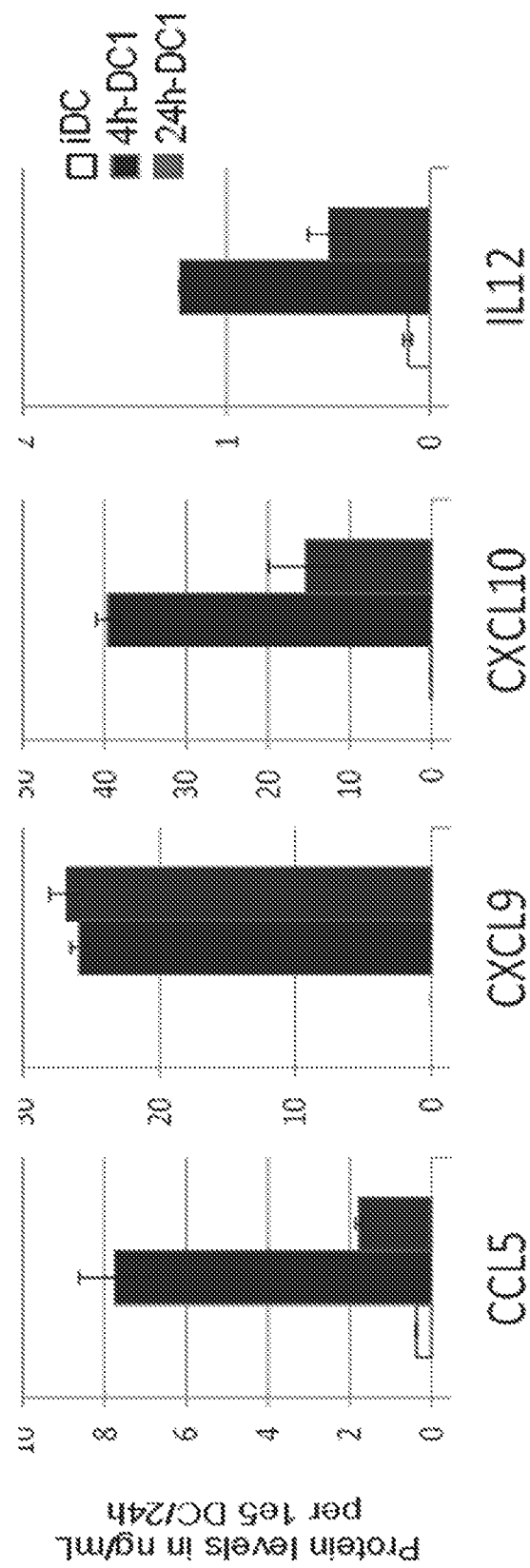

SHORT-TERM ACTIVATED DC1S AND METHODS FOR THEIR PRODUCTION AND USE

STATEMENT REGARDING FEDERALLY SPONSORED RESEARCH OR DEVELOPMENT

This invention was made with government support under CA132714 awarded by the National Institutes of Health. The government has certain rights in this invention.

BACKGROUND OF THE INVENTION

1) Field of the Invention

The fields of the invention are immunology, immunotherapy and treatment of cancer, premalignant lesions and chronic infections.

2) Description of Related Art

Cancer (or neoplastic disease) refers to cells that grows in an abnormal, unregulated way and that ultimately overwhelms a body system or organ. A "tumor" refers to any abnormal mass of cells and can be harmless or dangerous. A harmless tumor is called benign and does not contain cancerous cells whereas a dangerous tumor is called malignant because it contains cancerous cells.

Cancers are further divided into carcinomas, sarcomas, leukemias or lymphomas, according to the cell types that are involved. For example, cancers that develop in skin cells or cells lining or covering the internal organs are called carcinomas whereas sarcomas develop in bone, cartilage, fat, muscle, blood vessels or connective tissue. Cancers of the lymphatic system that develop in mature immune system cells are called lymphomas or leukemias.

The development of cancer might be seen as a failure of immune surveillance. However, not all cancers are naturally immunogenic, and even among those that are immunogenic, the uncontrolled rapid growth of a cancer may sometimes out-run a robust immune response. Further, recent evidence suggests that tumors themselves have the ability to thwart the development of effective immune responses against cancer antigens.

The immunosuppressive environments similar to those associated with cancer are also known to exist in the tissues chronically infected with several pathogens, in patients with tuberculosis, leprosy, as well as chronic infections with such viruses as HBV, HCV, HPV, EBV or CMV, many of them can convert into pre-malignant and malignant lesions.

Suboptimal homing of type-1 effector $CD8^+$ T cells (typically referred to as cytotoxic T cells; CTLs) to cancers constitutes a significant obstacle to clinical effectiveness of the spontaneously-occurring and therapeutically-induced immunity against cancer. The numbers of CTLs in multiple cancer types cancers have been shown to be an independent prognostic marker, with high numbers predicting a delayed time to cancer recurrence. See Yamada, et. al., Cancer Immunol. Immunother., 59:1543-1549 (2010); Anraku, et. al., J. Thorac. Cardiovasc. Surg., 135:823-829 (2008); Galon, et. al., Science, 313:1960-1964 (2006). In contrast, regulatory T cells (Tregs) are associated with poor cancer responses. See Clarke, et. al., PLoS ONE 1:e129 (2006); Michel, et. al., Br. J. Cancer, 99:1867-1873 (2008); Curiel, et. al., Nat. Med., 10:942-949 (2004).

Clinical studies in multiple forms of advanced cancer showed that PD1/PDL1 blockade is effective mainly in CTL-infiltrated and PD-L1/2-expressing tumors. See Tumeh, et. al., Nature, 515:568-571 (2014); Herbst, et. al., Nature, 515:563-567 (2014); Topalian, et. al., The N. Engl. J. Med., 366:2443-2454 (2012). These results provide rationale for enhancing intratumoral CTL accumulation and resulting PD-L1 expression to promote the therapeutic effects of checkpoint blockers, which, so far, have been poorly effective in some of the most frequent and deadly forms of cancer, such as colon cancer, breast cancer, prostate cancer or ovarian cancer.

Chemokines and their receptors are critical for T cell migration and homing into tissues during homeostasis, infection and acute or chronic inflammation. See Bonecchi, et. al., J. Exp. Med., 187:129-134 (1998); Hirai, et. al., J. Exp. Med., 193:255-261 (2001). Several studies have shown that CTL-expressed chemokine receptors CXCR3 and CCR5 are critical for CTL entry into tumors, which is guided by intra-tumoral expression of their respective chemokine ligands. High tumor tissue levels of CCL5/RANTES (ligand for CCR5), and CXCL9/MIG, CXCL10/IP10 and CXCL11/ITAC (three ligands for CXCR3) are associated with infiltration of CTLs in colorectal cancer (CRC), melanoma, and gastric cancer. See Musha, et. al., Int. J. Cancer, 116:949-956 (2005); Kunz, et. al., J. Pathol., 189:552-558 (1999); Ohtani, et. al., J. Pathol., 217:21-31 (2009). In contrast, high levels of CCL22 (ligand for CCR4) are associated with recruitment of Tregs and decreased patient survival. Curiel, et. al., Nat. Med., 10:942-949 (2004). Tumors frequently show elevated CCL22 and CXCL12 levels induced by an immunosuppressive prostaglandin $E_2$ ($PGE_2$), a COX2 product, abundant in the tumor microenvironment (TME) attracting Tregs and myeloid-derived suppressor cells (MDSCs), rather than CTLs, leading to highly biased Treg plus MDSC/CTL ratios in tumors. See Soumaoro, et. al., Clin. Cancer Res., 10:8465-8471 (2004); Williams, et. al., Ann. NY Acad Sci. 889:72-83 (1999); Obermajer, et. al., Cancer Res., 71:7463-7470 (2011). Recently published data also demonstrates the correlation between the intratumoral production of CCL5, CXCL9 and CXCL10 and local infiltration with $CD8^+GrB^+$ CTLs and the ability of these chemokines to attract spontaneously-arising and vaccination-induced CTLs to CRC tissues. See Muthuswamy, et. al., Cancer Res., 72:3735-3743 (2012).

Type-1 polarized dendritic cells (DC1s) and their subset, αDC1s, generated in the presence of type-1 IFNs, are a specialized type of dendritic cells (DCs), which combine a mature phenotype and high expression of co-stimulatory factors with an elevated, rather than exhausted, ability to produce IL-12p70. See Vieira, et al. J. Immunol. 164: 4507-4512 (2000) and Mailliard et. al., Cancer Res., 64(17): 5934-37 (2004). Activated DCs can secrete inflammatory cytokines such as IL-12, but then resist further stimulation (e.g., by CD40 or LPS) and no longer secrete high levels of cytokines such as IL-12 (e.g., IL-12p70) in a process termed "exhaustion." αDC1s have enhanced ability to cross-present tumor-derived antigens to $CD8^+$ T cells recognizing MHC class-I restricted tumor-related antigens in vitro and in vivo. See Giermasz, et. al., Cancer Immunol. Immunother., 58:1329-1336 (2009); Lee, et. al., J. Leukoc. Biol., 84(1): 319-25 (2008); Wieckowski, et. al., Prostate, 71:125-133 (2011). In addition, αDC1s effectively convert non-cytolytic $CD8^+$ T cells into high perforin- and granzyme B-expressing $CXCR3^{high}/CCR5^{high}$ CTLs, with high killer activity. See Watchmaker, et. al., J. Immunol., 184:591-597 (2010). In phase I/II study in 22 (19 evaluable) patients with recurrent high-grade malignant gliomas (expected time to progression of 2-4 months), who received systemic αDC1 vaccines (loaded with glioma-relevant peptide antigens) and polyinosinic-polycytidylic acid stabilized by lysine and carboxymethylcellulose (poly-ICLC; to induce intratumoral CXCL10) nine patients achieved Progression-free Survival (PFS) greater than 12 months, with two patients achieving complete radiologic responses and two additional patients undergoing partial (and sustained) responses (2 partial responses (PR) and one complete response (CR)) occurred after the original publication. See Okada, et. al., *J. Clin. Oncol.*, 29:330-336 (2011).

However, multiple cancers do not have clearly defined tumor rejection antigens, limiting the applicability of antigenic peptides as the source of tumor-relevant antigens. The use of autologous cancer cells as the source of tumor-relevant antigens bypasses this problem, and also allows treatment of the roughly 50% of cancer patients in the US population who do not express HLA-A2. However, autologous tumor-loaded DCs are logistically difficult to prepare and can only be administered at week 6 or later post-tumor resection. This is in part because production of the DC vaccine can only begin after tumor resection and verification of successful isolation of cancer cells, and generation and sterility testing of the DC vaccine requires at least 5 additional weeks. For this reason, autologous tumor-loaded DCs cannot be clinically used at the moment they are particularly needed to prevent the early repopulation of the peritoneal cavity with residual cancer cells which evade chemotherapy and surgery.

BRIEF DESCRIPTION OF THE DRAWINGS

FIG. 1A), TNFα (FIG. 1B), or lipopolysaccharide (LPS; FIG. 1C) along with IFNα, IFNγ, or both IFNα and IFNγ. The culture supernatants were tested for amounts of released CXCL10 (a CTL attractant) by ELISA. These results show that each of pI:C, TNFα, and LPS separately combined with either IFNα (type 1 IFN) alone or IFNγ (type 2 IFN) alone are insufficient to induce high levels of the CTL attractant CXCL10. However, each of pI:C, TNFα, and LPS separately combined with both IFNα and IFNγ results in synergistically high expression levels of CXCL10.

FIGS. 2A through 2D show that short-term ex vivo-activated αDC1s produce higher levels of IL-12 and Teff-attracting chemokines than 24-hour-matured DCs. Immature monocyte-derived DCs (200,000 cells/500 µl), generated as described in FIG. 1A through 1C, were exposed to nothing (left bar), or complete αDC1-inducing cocktail (IL-1β, TNFα, p-IC, IFNα, IFNγ) for 4 hours (middle bar) or 24 hours (right bar). In all cases, DC cultures were washed and re-cultured in fresh medium for an additional 24 hours. The supernatants were tested for amounts of released CCL5 (FIG. 2A), CXCL9 (FIG. 2B), CXCL10 (FIG. 2C), and IL-12p70 (FIG. 2D) by ELISA.

In FIG. 5A, B6 mice (n=10 per group) were injected i.p. with high dose ($3\times10^6$ cells) MC38 peritoneal colorectal cancer cells (day 0) and 3 doses (days 3, 6, 9) of αPD-1 mAb (Rmp1-14, BioXCell, 90 µg/mouse) or saline. Similar PD-1 results in this model were observed in two additional experiments. These results show that treatment of peritoneal colorectal cancer with αPD-1 mAb alone results in only minor improvement in mouse survival, though the results are statistically significant. In FIG. 5B, B6 mice (n=10 per group) were injected i.p. with high dose ($3\times10^6$ cells) MC38 peritoneal colorectal cancer cells (day 0). Control mice received no further injections. On days 7 and 10, both test groups (non-control mice) received two i.p. doses of tumor-unloaded $3\times10^5$ ST-αDC1s ($\alpha DC^{unload}$i.p.). Further, 3 doses of αPD-1 mAb (Rmp1-14; $\alpha DC^{unload}$i.p.+αPD1 Ab group) or saline ($\alpha DC^{unload}$i.p. group) were also injected on days 3, 6, and 9. IACUC approved criteria were used to determine the day of euthanasia. These results show that a combination therapy of αDC1 cells and αPD-1 mAb result in significant improvement in mouse survival. P>0.0001: DC+ PD-1 vs control or DC group.

DETAILED DESCRIPTION OF THE INVENTION

Figure 1A:
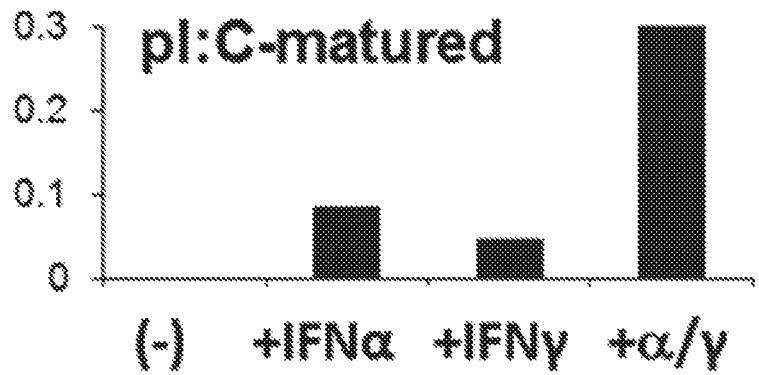
FIGS. 1A through 1C show that a combination of Type-1 and Type-2 interferons (IFNs), or the combination of IFNs with inflammatory factors, synergistically induce high levels of effector T-cell (Teff)-attracting chemokines. Immature monocyte-derived DCs were generated from monocytes in six-day cultures (approx. $5\times10^5$ cells/well) supplemented with rhu granulocyte macrophage colony-stimulating factor (GM-CSF; 1,000 IU/mL) and interleukin 4 (IL-4; 1,000 IU/mL). See Mailliard et. al., Cancer Res., 64(17):5934-37 (2004). Immature monocyte-derived DCs (200,000 cells/500 µl) were exposed for 24 hours to polyinosinic:polycytidylic acid (pI:C.

Provided herein are methods of treating cancer, infections and premalignant lesions using short-term activated alpha type 1-polarized dendritic cells (termed "ST-αDC1s") compositions comprising ST-αDC1s, and methods for making ST-αDC1s. It is a surprising finding of the present invention that short term exposure of dendritic cells to a combination of one or more of a type 1 interferon (i.e., IFNα, IFNβ, IFN-κ, IFNω and IFNν) and one or more of a type 2 interferon (IFNγ) results in dendritic cells that produce increased levels of IL-12, CCL5, CXCL9, and/or CXCL10 as compared to dendritic cells having a longer term exposure. The ST-αDC1s of the present invention can produce increased levels of CTL, Th1, and NK cell attracting chemokines even in the presence of suppressive tumor microenvironments (TME). Since intratumoral accumulation of CTLs is generally known to lead to enhanced survival of cancer patients and to be needed for the responsiveness to immune checkpoint blockers (a group of immune inhibitors which includes Program Death-1 (PD1), Cytotoxic T-Lymphocyte-Associated protein 4 (CTLA-4), Lymphocyte-Activation Gene 3 (LAG3) inhibitor, T-cell Immunoglobulin domain and Mucin domain 3 (TIM-3) inhibitor, V-domain Ig Suppressor of T cell Activation (VISTA) inhibitor, B and T Lymphocyte Attenuator (BTLA) inhibitor, which interact with their ligands in tumor microenvironments and activated lymph nodes), vaccines and adoptive T cell therapies (including ACT with CAR-T cells, TCR-transgenic T cells, or ex vivo-expanded NK cells), ST-DC1s can be used as self-standing immunotherapeutic factors or in combination immunotherapies against cancer. Further, as it is known that early stages of DC activation are associated with high antigen uptake and that simultaneous exposure of DCs to type-1-polarized factors and tumor cells results in enhanced antigen uptake and cross-presentation, intratumorally-injected ST-DC1s may be able to serve as inducers of CTL and Th1 responses against multiple patient-specific tumor antigens, offering a new treatment option against multiple tumors which lack defined tumor rejection antigens.

Definitions

Terms used throughout this application are to be construed with ordinary and typical meaning to those of ordinary skill in the art. However, Applicants desire that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The term "ST-αDC1" refers herein to a dendritic cell (DC) that results from the exposure of an immature DC to one or more of a type 1 interferon (i.e., IFNα, IFNβ, IFN-κ, IFNω and IFNν) and one or more of a type 2 interferon (IFNγ) for less than 16 hours. In some embodiments, the ST-αDC1 results from the exposure of an immature DC to one or more of a type 1 interferon and one or more of a type 2 interferon for less than 16 hours, less than 12 hours, less than 8 hours, or less than 4 hours. In further embodiments, the ST-αDC1 results from the exposure of an immature DC to one or more of a type 1 interferon and one or more of a type 2 interferon for between 1 hour and 12 hours, between 1 hour and 8 hours, or between 1 hour and 4 hours. In still further embodiments, the ST-αDC1 results from the exposure of an immature DC to one or more of a type 1 interferon and one or more of a type 2 interferon for between 2 hours and 12 hours, between 2 hours and 8 hours, or between 2 hours and 4 hours. In yet further embodiments, the ST-αDC1 results from the exposure of an immature DC to one or more of a type 1 interferon and one or more of a type 2 interferon for between 3 hours and 12 hours, between 3 hours and 8 hours, or between 3 hours and 4 hours. In some embodiments, the ST-αDC1 results from the exposure of an immature DC one or more of a type 1 interferon and one or more of a type 2 interferon for approximately 1 hour, 2 hours, 3 hours, or 4 hours.

In other embodiments, the ST-αDC1 results from the exposure of an immature DC one or more of a type 1 interferon and one or more of a type 2 interferon in addition to tumor necrosis factor alpha (TNFα), interleukin 1 beta (IL-1β), polyinosinic:polycytidylic acid (referred to herein as poly-I:C, pI:C or p-IC), granulocyte-macrophage colony-stimulating factor (GM-CSF), and/or lipopolysaccharide (LPS). In some embodiments, the immature DC is exposed to one or more of TNFα, IL-1β, poly-I:C, GM-CSF, and LPS before exposure to the one or more of a type 1 interferon and one or more of a type 2 interferon.

The term "administering" refers to an administration that is oral, topical, intravenous, subcutaneous, transcutaneous, transdermal, intramuscular, intra joint, intra-tumor, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrastemal, intrathecal, intrahepatic, intralesional, and intracranial injections or infusion techniques.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

The term "cancer" is used herein to address any neoplastic disease, and is not limited to epithelial neoplasms (surface and glandular cancers; such a squamous cancers or adenomas). The term "cancer" is used here to describe both solid tumors and hematologic malignancies, including epithelial (surface and glandular) cancers, soft tissue and bone sarcomas, angiomas, mesothelioma, melanoma, lymphomas, leukemias and myeloma. The term "tumor" is used herein to describe a mass or collection of cancer cells.

The term "precancerous condition" includes any condition which may develop into a cancer including, but not limited to, chronic infections (including, but not limited to HIV, HPV, Hepatitis B and Hepatitis C, EBV, CMV, *M. tuberculosis*, and intracellular bacteria and parasites), as well as chronic inflammatory states, including inflammatory bowel disease (including Crohn's and ulcerative colitis), Barrett's esophagus, Ductal carcinoma in situ (CIS), cervical intraepithelial neoplasia (CIN), vulvar intraepithelial neoplasia (VIN), chronic pancreatitis, chronic hepatitis (viral and non-viral etiologies), lymphoproliferative syndromes, chronic gastritis, chronic esophagitis, chronic obstructive pulmonary disease (COPD) and globulinopathies.

The terms "cell," "cell line," and "cell culture" include progeny. It is also understood that all progeny may not be precisely identical in DNA content, due to deliberate or inadvertent mutations.

A "composition" is intended to include a combination of active agent or agents (for example, one or more ST-αDC1s) and another compound or composition, inert (for example, a detectable agent or label) or active, such as an adjuvant.

As used herein, the term "comprising" is intended to mean that the compositions and methods include the recited elements, but not excluding others. "Consisting essentially of"

when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative." Various controls within the scope of the present invention are described in more detail below. In some embodiments, the control comprises an immature DC cell that is exposed for at least 24 hours to the one or more of a type 1 interferon and the one or more of a type 2 interferon applied to the non-control immature DC cell.

An "effective amount" is an amount sufficient to effect beneficial or desired results. An effective amount can be administered in one or more administrations, applications or dosages.

As used herein, "gene expression" and "protein expression" refer to the process by which polynucleotides are transcribed into mRNA and the process by which the transcribed mRNA is subsequently being translated into peptides, polypeptides, or proteins, respectively. If the polynucleotide is derived from genomic DNA, expression may include splicing of the mRNA in a eukaryotic cell. "Gene overexpression" refers to the overproduction of the mRNA transcribed from the gene, at a level that is about 2.5 times higher, about 5 times higher, or about 10 times higher than the expression level detected in a control sample. "Protein overexpression" includes the overproduction of the protein product encoded by a gene at a level that is about 2.5 times higher, about 5 times higher, or about 10 times higher than the expression level detected in a control sample.

An "immature dendritic cell" is defined herein as a dendritic cell having lower CD80, CD86 and CCR7 expression than a mature or a short-term mature dendritic cell. In some embodiments, an immature dendritic cell (DC) can be generated from a monocyte. In some embodiments, the monocyte is exposed to rhu granulocyte macrophage colony-stimulating factor (GM-CSF), interleukin 4 (IL-4), or combinations thereof to generate the immature DC. In some embodiments, the monocyte is exposed to GM-CSF in an amount ranging from 1 IU/mL to 10,000,000 IU/mL, from 10 IU/mL to 1,000,000 IU/mL, from 100 IU/mL to 100,000 IU/mL, from 100 IU/mL to 10,000 IU/mL, or in an amount of about 1000 IU/mL. In some embodiments, the monocyte is exposed to IL-4 in an amount ranging from 1 IU/mL to 10,000,000 IU/mL, from 10 IU/mL to 1,000,000 IU/mL, from 100 IU/mL to 100,000 IU/mL, from 100 IU/mL to 10,000 IU/mL, or in an amount of about 1000 IU/mL. In some embodiments, the monocyte is exposed to GM-CSF, IL-4, or combinations thereof for at least one day, at least two days, at least three days, at least four days, at least five days, at least six days, at least seven days, at least eight days, at least nine days, at least ten days, or more.

A "mature dendritic cell" is defined herein as a dendritic cell having high CD80, CD86 and CCR7 expression. As used herein "surface expression" refers to the process by which polypeptides are translocated to the surface of a cell such that at least a portion of the polypeptide is located at the exterior of the cell surface. "Surface overexpression" includes an increase in the amount of a particular polypeptide at the exterior surface of a cell, at a level that is about 2.5 times higher, about 5 times higher, or about 10 times higher than the surface expression level detected in a control sample. In some embodiments, "surface expression" relates to the expression of a receptor that binds to a compound at the cell surface exterior, such as, for example, an interleukin receptor.

The term "identity" shall be construed to mean the percentage of nucleotide bases or amino acid residues in the candidate sequence that are identical with the bases or residues of a corresponding sequence to which it is compared, after aligning the sequences and introducing gaps, if necessary to achieve the maximum percent identity for the entire sequence, and not considering any conservative substitutions as part of the sequence identity. Neither N- nor C-terminal extensions nor insertions shall be construed as reducing identity. A polynucleotide or polynucleotide region (or a polypeptide or polypeptide region) that has a certain percentage (for example, about 80%, about 85%, about 90%, or about 95%) of "sequence identity" to another sequence means that, when aligned, that percentage of bases (or amino acids) are the same in comparing the two sequences. This alignment and the percent sequence identity can be determined using software programs known in the art. In one embodiment, default parameters are used for alignment. In one embodiment a BLAST program is used with default parameters. In one embodiment, BLAST programs BLASTN and BLASTP are used with the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

"Mammal" for purposes of treatment refers to any animal classified as a mammal, including human, domestic and farm animals, nonhuman primates, and zoo, sports, or pet animals, such as dogs, horses, cats, cows, etc.

A "pharmaceutical composition" is intended to include the combination of an active agent with a pharmaceutically acceptable carrier, inert or active, making the composition suitable for diagnostic or therapeutic use in vivo or ex vivo.

The term "pharmaceutically acceptable carrier" means a carrier or excipient that is useful in preparing a pharmaceutical composition that is generally safe and non-toxic, and includes a carrier that is acceptable for veterinary and/or human pharmaceutical use. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below. The pharmaceutical compositions also can include preservatives. A "pharmaceutically acceptable carrier" as used in the specification and claims includes both one and more than one such carrier.

The terms "pharmaceutically effective amount," "therapeutically effective amount," and "therapeutically effective dose" refer to the amount of a composition such as an ST-αDC1 cell composition that will elicit the biological or medical response of a tissue, system, animal, or human that is being sought by the researcher, veterinarian, medical doctor or other clinician. In some embodiments, a desired response is a treatment of a cancer. In some instances, a desired biological or medical response is achieved following administration of multiple dosages of the composition to the subject over a period of days, weeks, or years. The terms "pharmaceutically effective amount," "therapeutically effective amount," and "therapeutically effective dose" include that amount of a composition such as an ST-αDC1 cell composition that, when administered, is sufficient to prevent development of, or alleviate to some extent, one or more of the symptoms of the condition or disorder being treated. The therapeutically effective amount will vary depending on the composition, such as the ST-αDC1 cell composition, the disorder or conditions and its severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of an ST-αDC1 cell composition includes an amount that is sufficient to prevent development of, suppress the growth of, or reduce the numbers of, one or more cancers or tumors. A pharmaceutically or therapeutically effective amount or dose of an ST-αDC1 cell composition also includes an amount that is sufficient to treat a precancerous condition or chronic infection.

The terms "prevent," "preventing," "prevention," and grammatical variations thereof as used herein, refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

To "suppress" tumor growth indicates a curtailment of growth state when compared to growth without contact with an ST-αDC1 cell composition described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

The terms "treat," "treating," "treatment" and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. In some instances, the terms "treat," "treating," "treatment" and grammatical variations thereof, include partially or completely reducing the size of a solid tumor or reducing the number of solid tumors as compared with prior to treatment of the subject or as compared with the incidence of such symptom in a general or study population.

DETAILED DESCRIPTION

Figure 1B:
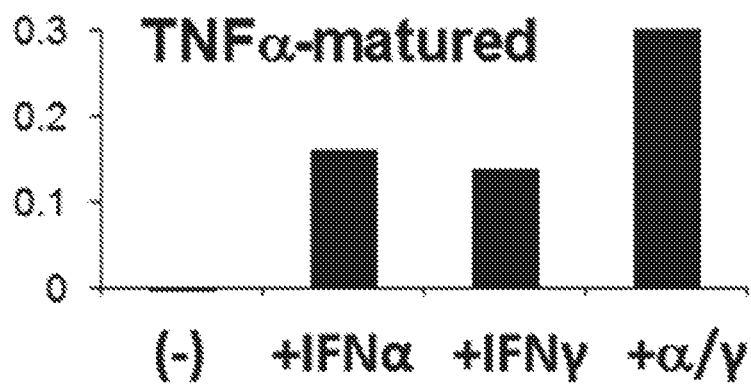
Figure 1C:
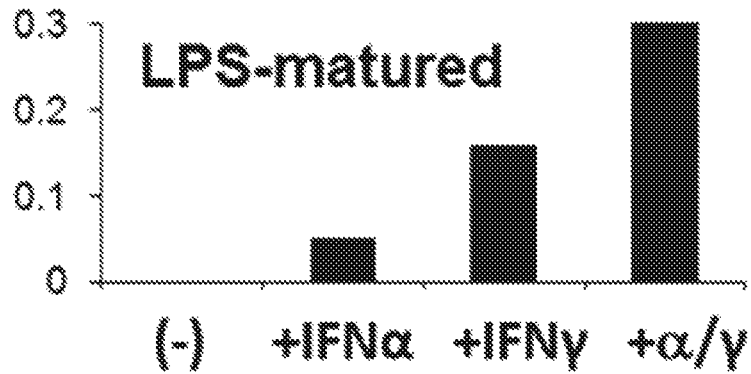

Provided herein are methods of treating cancer, and in some embodiments, solid tumors, using ST-αDC1s, short-term activated dendritic cells. The data provided herein in FIG. 1 demonstrate that type-1 and type-1 interferons act synergistically when used to activate human DCs. The data presented in FIG. 2 demonstrate that human 4 hour-matured ST-αDC1s produce much higher levels of CTL-attractants than fully mature αDC1s, currently used as therapeutic vaccines.

Figures 3A, 3B, 3C:
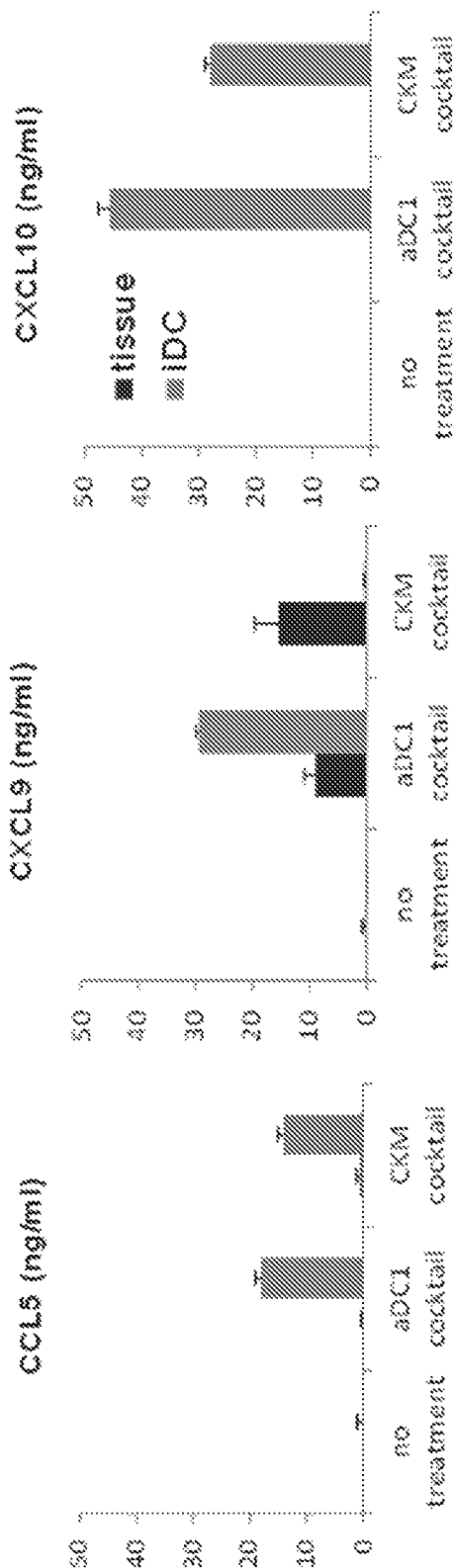
FIGS. 3A through 3C show that human ST-αDC1s produce higher levels of Teff-attractants than colorectal cancer (CRC) tissues directly exposed to αDC1-inducing factors. Omental CRC tissue explants (ca 150 µg/500 µl) or immature monocyte-derived DCs (200,000 cells/500 µl) were exposed for 4 hours to either complete αDC1-inducing cocktail (IL-1β, TNFα, pI:C, IFNα, IFNγ) or to a chemokine-modulating cytokine cocktail ("CKM": pI:C, IFNα and Celecoxib). In each case, cells/tissues were washed after 4 hours and re-cultured for an additional 24 hours. The supernatants were tested for amounts of released CCL5 (FIG. 3A), CXCL9 (FIG. 3B), and CXCL10 (FIG. 3C) by ELISA. Note the advantage of αDC1 cocktail over CKM in inducing CXCL9, as well as CXCL10 and CCL5, when used to activate DCs, rather than tumor tissue. Similar advantage was observed when isolated tumor cells were used (data not shown).
Figure 4A:
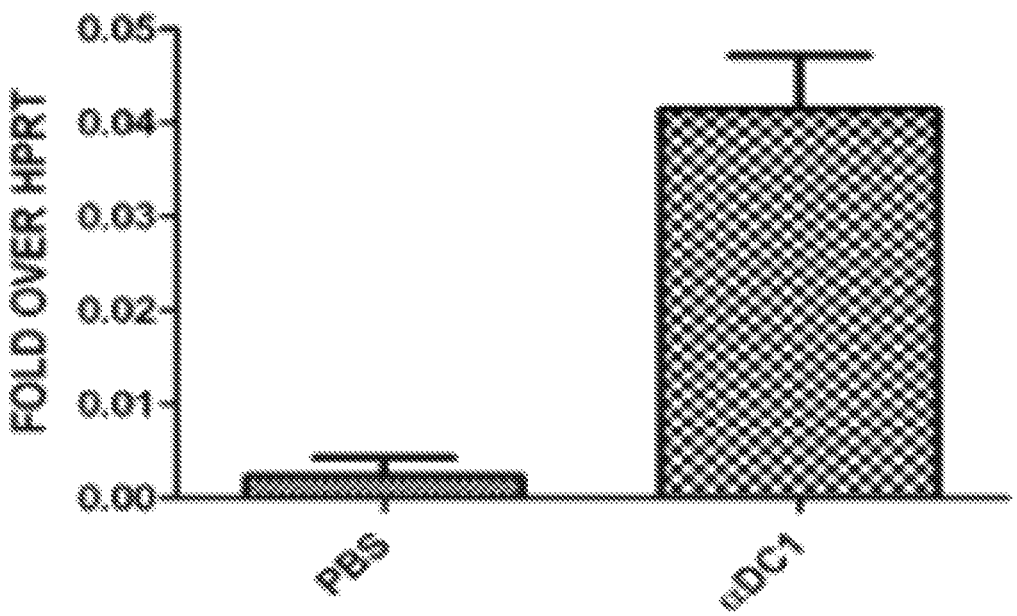
FIGS. 4A through 4H show that tolerability and efficacy of i.p.-injected mouse ST-αDC1s in promoting local effector-type immunity in a mouse model of peritoneal colorectal cancer (i.p. MC38 model). DCs were isolated from the spleens of Flt3-treated B6 animals as described in Giermasz, et. al., *Cancer Immunol. Immunother.*, 58:1329-1336 (2009); Budiu, et. al., *Oncogene*, 32:3664-75 (2012). DCs were then activated ex-vivo (4 hours only) with IFNα (1000 U/ml), IFNγ (500 U/ml), p-IC (10 µg/ml), TNFα (5 ng/ml), IL1β (25 ng/µl), and GM-CSF (1000 U/ml). αDC1s were washed and delivered i.p. (300,000 αDC1s per mouse) to MC38 bearing mice (5 mice per group). No signs of toxicity were observed, and the mice were sacrificed after 48 hours. Expression of CTL, Th1 and NK cell marker in i.p. ascites cells (FIGS. 4A through 4G), and solid tumor tissues (FIG. 4H) was tested by Taqman. The measured cell marker mRNA included CXCL10 (FIG. 4A), CCL5 (FIG. 4B), CD8 (FIG. 4C), NKP46 (FIG. 4D), IFNγ (FIG. 4E), Granzyme B (FIG. 4F), and Perforin (FIG. 4G), each in peritoneal lavage fluid, and Perforin (FIG. 4H) in solid tumor tissue. In each case, increased amounts of CTL, Th1 and NK cell markers were observed, indicating accumulation of these cell types.
Figure 4B:
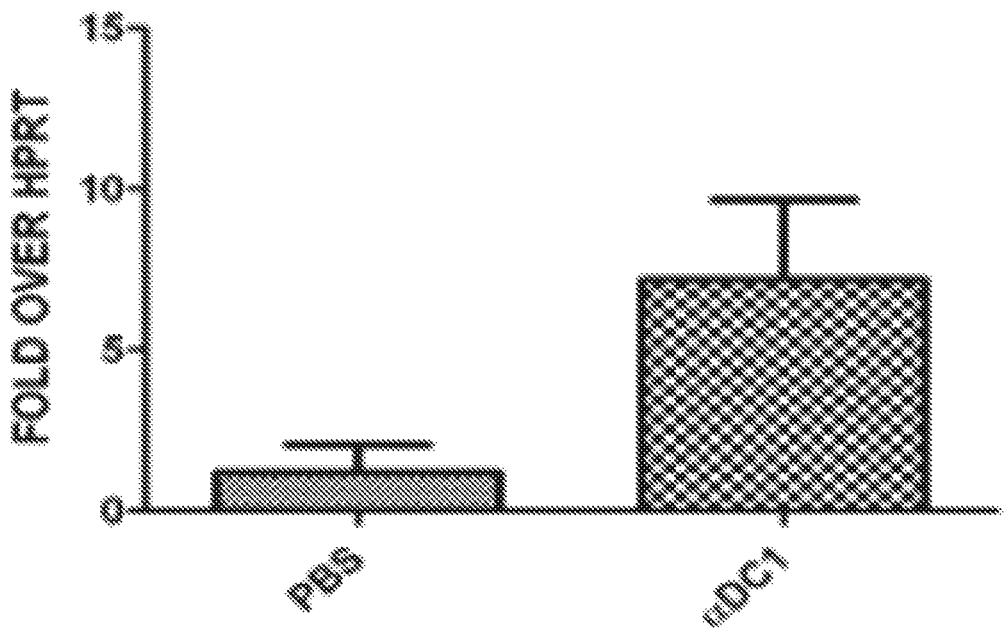
Figure 4C:
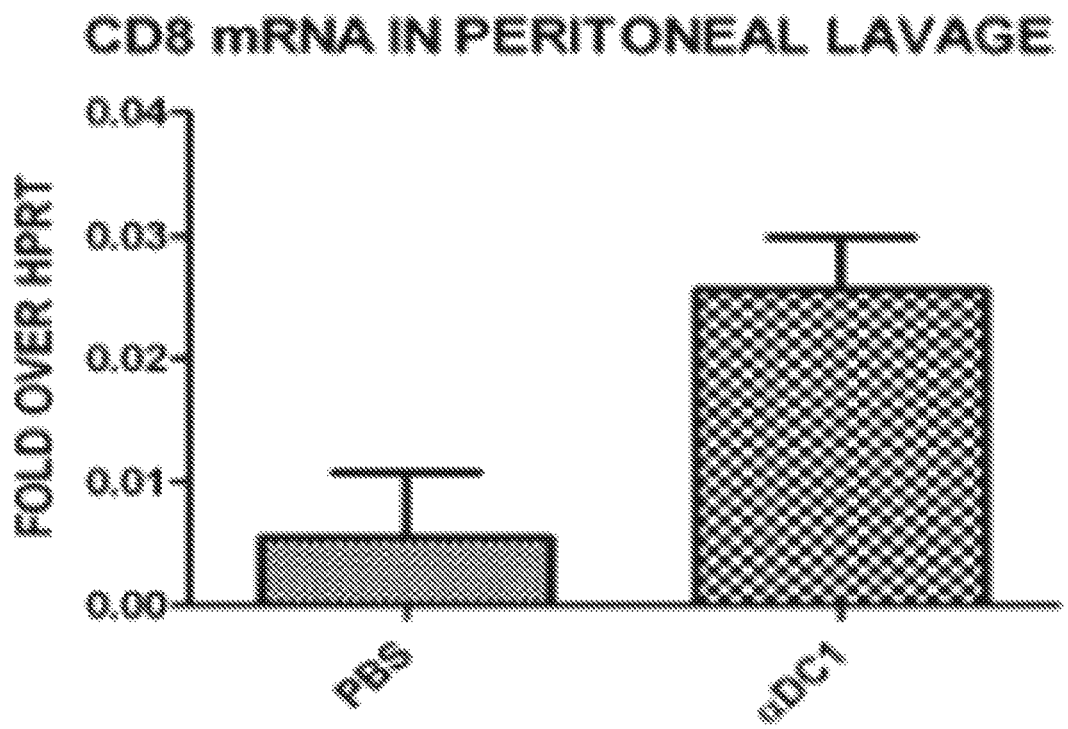
Figure 4D:
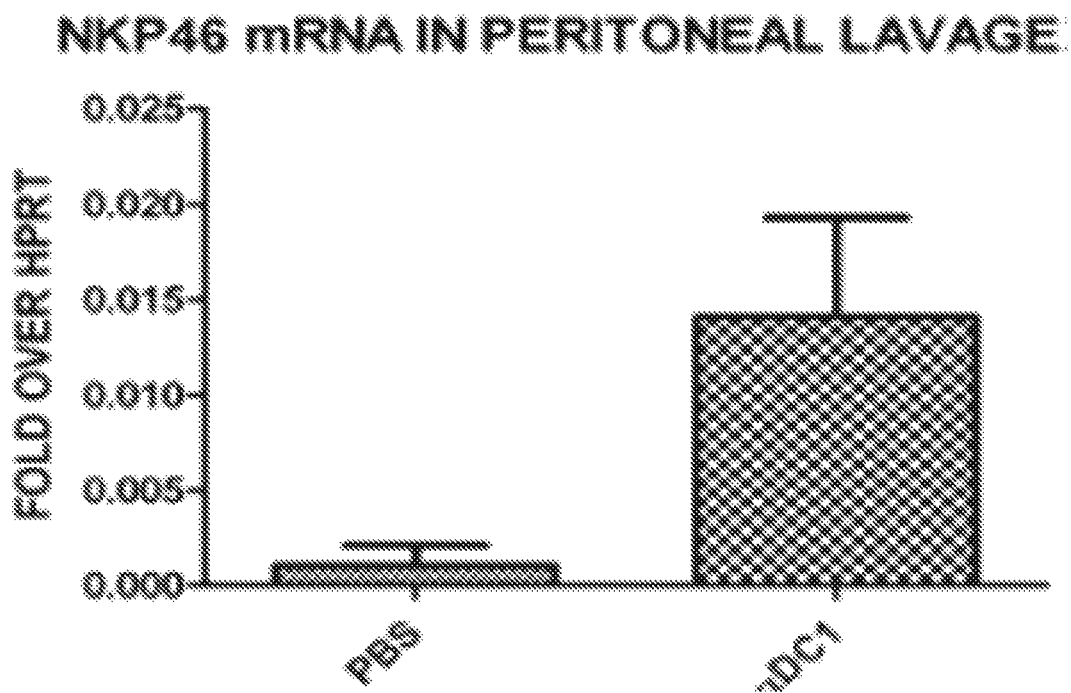
Figure 4E:
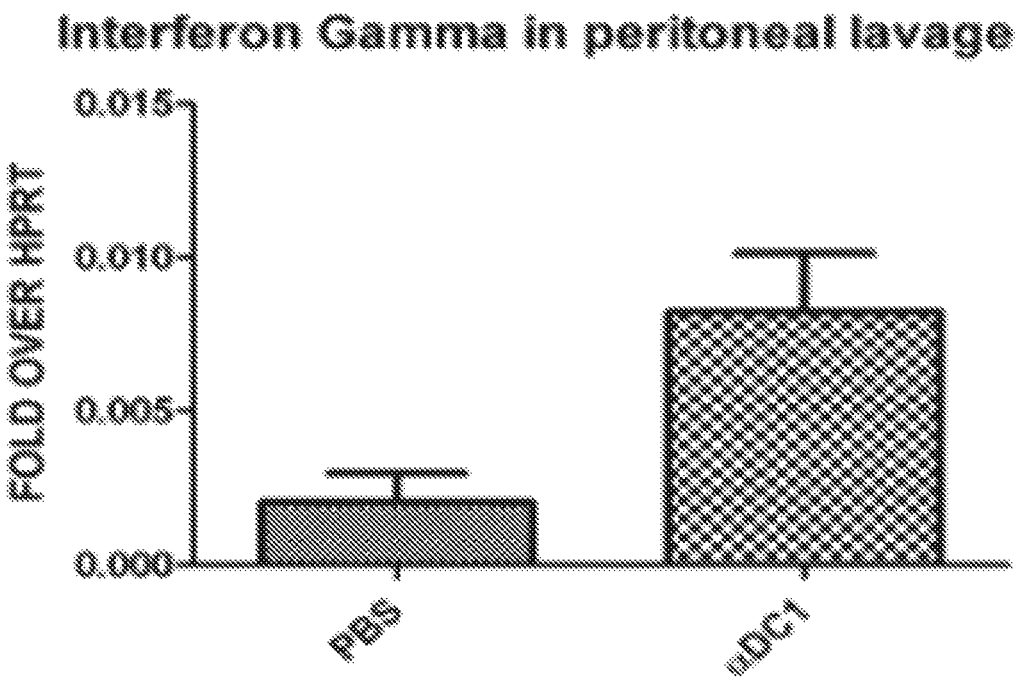
Figure 4F:
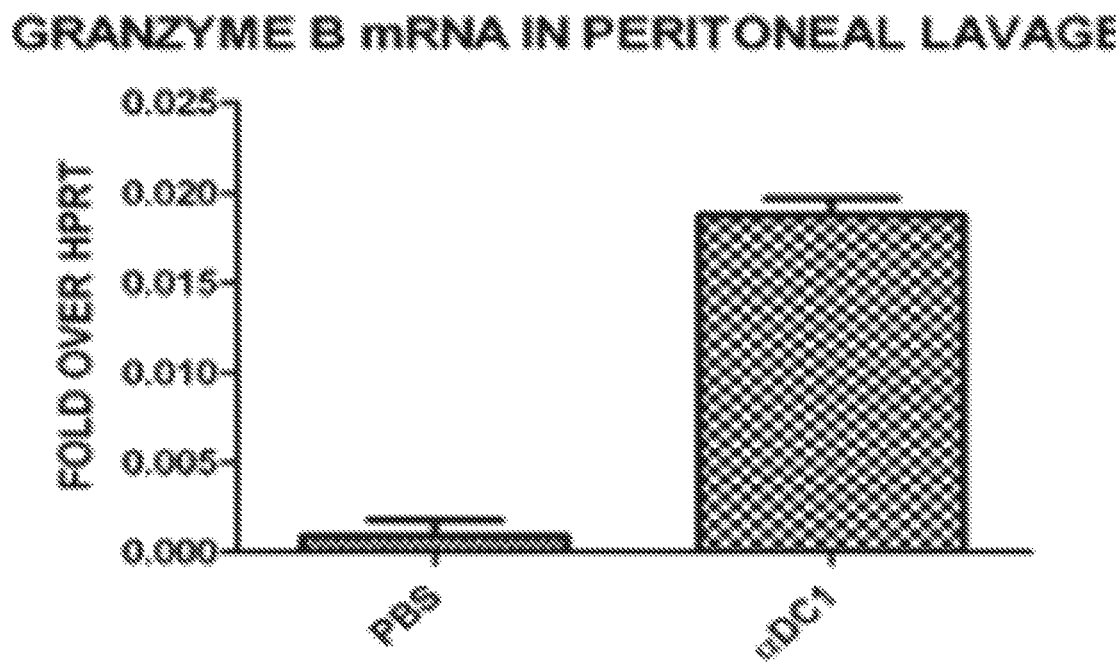
Figure 4G:
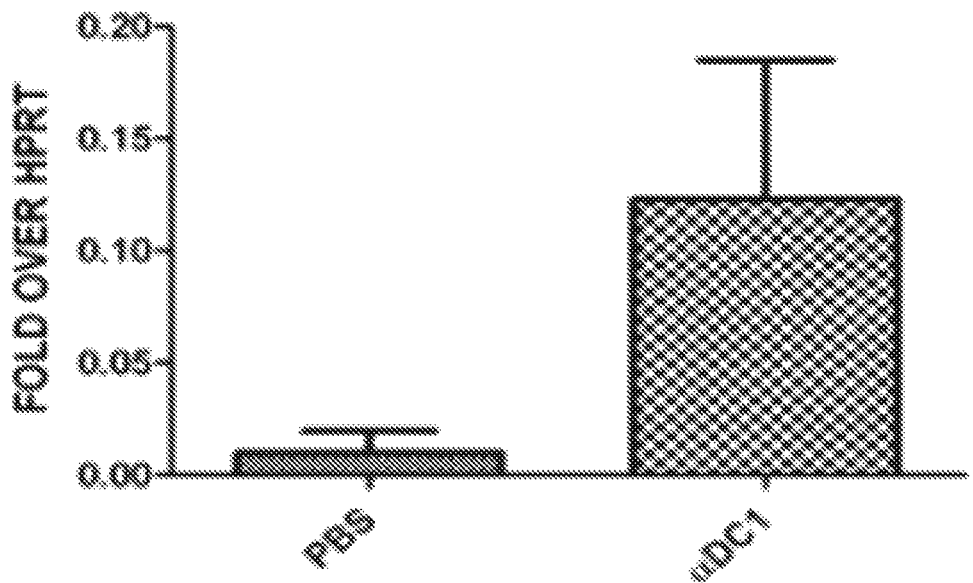
Figure 4H:
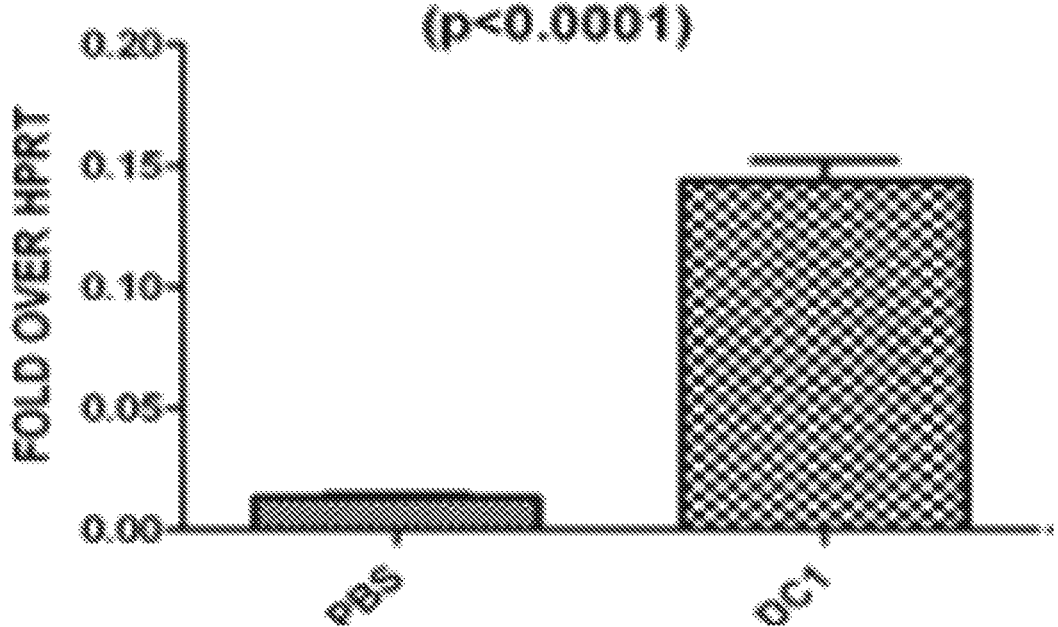

Importantly, ex vivo-pre-activated ST-αDC1s produce significantly more CTL attractants than tumor tissues directly exposed to the same αDC1-inducing cytokine cocktail or to the three-component chemokine-modulating cocktail (CKM: poly-I:C, IFNα and COX2 blocker) that are used as a tumor microenvironment modulator in ongoing clinical trials in CRC (FIG. 3). See Muthuswamy, et. al., *Cancer Res.*, 72:3735-3743 (2012). Therefore, ST-αDC1s can correct immune dysfunction and enhance immune surveillance, even in the CTL-deficient environments of advanced cancer.

Figures 5A, 5B:
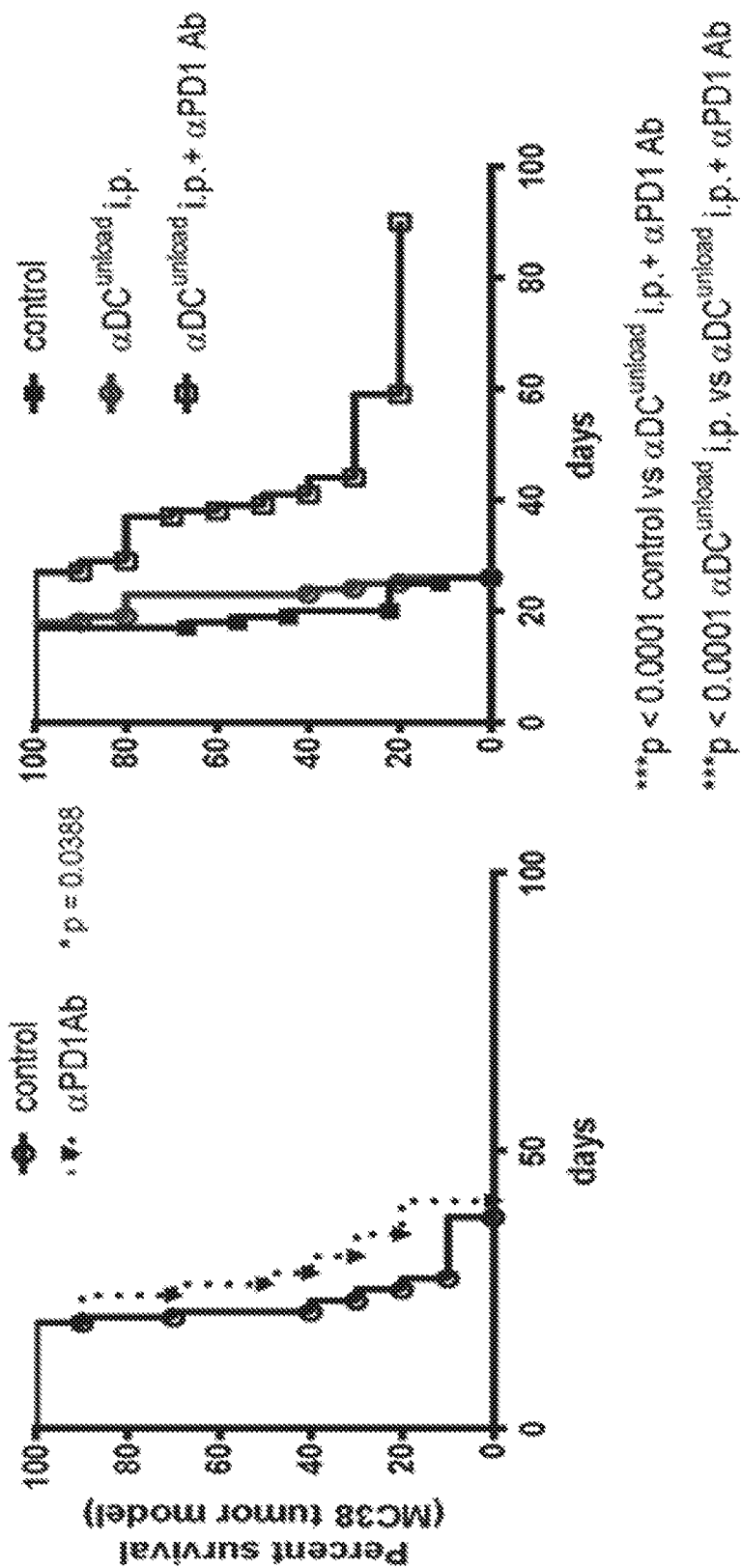
FIGS. 5A and 5B show ST-αDC1 cells promote therapeutic effects of PD-1 blockade in high-volume checkpoint-resistant mouse peritoneal cancer (i.p. MC38).

The ability of ST-αDC1s to function in vivo was demonstrated in the mouse i.p. MC38 model of PC where it was observed that mouse ST-αDC1s enhance the expression of CTL attractants and type-1 immune markers (CD8, IFNγ, GrB, Perforin, NKp46) in tumor ascites and solid fractions of i.p. tumors (FIG. 4). Reflecting prior clinical studies in CRC, it was observed that PD-1 blockade has only marginal therapeutic efficacy against high-dose i.p. MC38 (a model of disseminated CRC; FIG. 5A). However, PD-1 blockade combined with i.p. administration of ST-αDC1s (not loaded with cancer cells) strongly enhanced the antitumor effects of PD-1 blockade in this challenging model, where each component alone was only weakly (although significantly; $p<0.05$) effective (FIG. 5B). These data show that ST-αDC1s can increase the numbers of CTLs in mouse tumors (FIG. 4.), and can enhance the clinical activity of checkpoint blockers and, potentially, other forms of immunotherapy, such as adoptive T cell therapies (ACT). The i.p. administration of ST-αDC1, alone or with a PD-1 blockade, lacked any detectable toxicity in all mouse experiments.

The ST-αDC1s described herein are an incompletely-mature form of polarized DC's which are activated ex vivo by synergistically-acting mediators of antiviral responses with no antigen loading, which are specialized in supporting anti-cancer immunity at the tumor sites by attracting effector immune cells (CTLs and Th1 cells) and NK cells taking up and cross-presenting tumor-derived antigens in vivo and selectively attracting effector CTLs, Th1- and NK cells to tumors. Intratumoral (i.t.) injection of ST-αDC1s without their ex vivo loading with tumor enhances local immune surveillance in the perioperative period, when it is particularly needed. In contrast to immunization with defined peptide antigens, injection of ST-αDC1s is widely applicable to different cancers and patients, independent of the patient HLA type, tumor histology, mutational status, or the availability of previously-defined tumor-rejection antigens. Importantly, local administration of ST-αDC1s offers multi-pronged immune-stimulatory action by enhancing both induction and effector immunity. Using ST-αDC1s to promote intratumoral accumulation of CTLs and sensitize tumors to anti-PD1 therapy are both novel approaches.

Methods of Treating Cancer

Accordingly, provided herein are methods of using the ST-αDC1s for the treatment of a cancer. Provided herein is a method of treating a cancer in a subject comprising administering to the subject a pharmaceutically effective amount of an ST-αDC1, or ST-αDC1 population, as described herein.

The methods are useful for the treatment of a wide array of cancer types in part because the methods can result in increased anti-cancer or anti-tumor CTL recruitment or infiltration facilitated by increased production of CTL attractants by ST-αDC1s. Non-limiting examples of cancers that can be treated with these methods include Acute granulocytic leukemia, Acute lymphocytic leukemia, Acute myelogenous leukemia (AML), Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma, Bile duct cancer, Bladder cancer, Bone cancer Bone marrow cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia (CLL), Chronic myelogenous leukemia (CML), Colon cancer, Colorectal cancer, Craniopharyngioma, Cutaneous lymphoma, Cutaneous melanoma, Diffuse astrocytoma, Ductal carcinoma in situ (DCIS), Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, Gallbladder cancer, Gastric cancer, Gastrointestinal cancer, Gastrointestinal carcinoid cancer, Gastrointestinal stromal tumors (GIST), Germ cell tumor, Gestational Trophoblastic Disease (GTD), Glioblastoma multiforme (GBM), Glioma, Hairy cell leukemia, Head and neck cancer, Hemangioendothelioma, Hodgkin's lymphoma, Hypopharyngeal cancer, Infiltrating ductal carcinoma (IDC), Infiltrating lobular carcinoma (ILC), Inflammatory breast cancer (IBC), Intestinal Cancer, Intrahepatic bile duct cancer, Invasive/infiltrating breast cancer, Islet cell cancer, Jaw/oral cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma, Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Mycosis Fungoides, Myelodysplastic Syndrome, Nasal cavity cancer, Nasopharyngeal cancer, Neck cancer, Neuroblastoma, Neuroendocrine tumors (NETs), Non-Hodgkin's lymphoma, Non-small cell lung cancer (NSCLC), Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system (CNS) lymphoma, Prostate cancer, Rectal cancer, Renal cell carcinoma, Renal pelvis cancer, Rhabdomyosarcoma, Salivary gland cancer, Sarcoma, Sinus cancer, Skin cancer, Small cell lung cancer (SCLC), Small intestine cancer, Soft tissue sarcoma, Spinal cancer, Spinal column cancer, Spinal cord cancer, Spinal tumor, Squamous cell carcinoma, Stomach cancer, Synovial sarcoma, T-cell lymphoma, Testicular cancer, Throat cancer, Thymoma/thymic carcinoma, Thyroid cancer, Tongue cancer, Tonsil cancer, Transitional cell cancer, Transitional cell cancer, Triple-negative breast cancer, Tubal cancer, Tubular carcinoma, Ureteral cancer, Urethral cancer, Uterine adenocarcinoma, Uterine cancer, Uterine sarcoma, Vaginal cancer, Vulvar cancer, Wilms tumor, Waldenstrom macroglobulinemia, etc., and combinations thereof. In some embodiments, the cancer is selected from the group consisting of colorectal cancer, ovarian cancer, breast cancer, prostate cancer, and multiple myeloma.

In some embodiments of the method of treatment, the cancer is a tumor. Tumors can arise in any tissue including, but not limited to, breast, head and neck, lung, airways, prostate, colon, brain, cervix, uterus, ovaries, fallopian tubes, pancreas, esophagus, stomach, gastrointestinal tract, genitourinary tract, skin, liver, kidney, bone, soft connective tissue, central and peripheral nervous system and endocrine and exocrine tissues. In some embodiments, the tumor is malignant. In some embodiments, the tumor is solid.

The subject of treatment according to the methods described herein may be any animal, mammal, warm-blooded mammal or human. In one embodiment, the subject of treatment is a human. The subject may be diagnosed with a condition for which the methods are useful (e.g., a cancer or tumor) or be suspected by a clinician of having such a condition.

ST-αDC1 cells can be obtained from manipulations (e.g., exposure to activating agents, immunomodulators, etc.) performed on immature dendritic cells (DCs). The immature DC can be any DC capable of conversion to a ST-αDC1 cell, and thus typically requires that the DC be fully immature or partially immature (e.g., the DC is not completely mature). Immature DCs and production of immature DCs are described herein and further in Vieira, et al., *J. Immunol.*, 164: 4507-4512 (2000); Mailliard et. al., *Cancer Res.*, 64(17):5934-37 (2004), Giermasz, et. al., *Cancer Immunol. Immunother.*, 58:1329-1336 (2009); and Budiu, et. al., *Oncogene*, 32:3664-75 (2012). The immature DC can be obtained from a stock cell bank, but is typically obtained from the subject. Alternatively, the immature DC can be a cell which results from reprogramming a stem cell (e.g., a tissue stem cell or an induced pluripotent stem cell) or more differentiated progenitor cells from bone marrow or a lymphoid organ of the subject to express an immature DC phenotype.

The methods can include exposing an immature DC cell or cell population to one or more type 1 interferons, thereby resulting in one or more ST-αDC1 cells or cell populations. Suitable type 1 interferons include IFNα, IFNβ, IFN-κ, IFNω and IFNν. In non-human animals, type 1 interferons can also include IFNε, IFNτ, IFNδ, and IFNζ.

The methods can include exposing an immature DC cell or cell population to one or more type 2 interferons, thereby resulting in one or more ST-αDC1 cells or cell populations. Suitable type 2 interferons include IFNγ. In non-human animals, type 2 interferons can also include IFNγ1 and IFNγ2.

Exposure of an immature DC cell or cell population to a type 1 interferon can be performed prior to, subsequent to, or concurrent with exposure to a type 2 interferon. In some embodiments, the immature DC cell or cell population is exposed to one or more type 1 interferon and one or more type 2 interferon for substantially the same time period.

In some embodiments, the methods can include exposing an immature DC cell or cell population to one or more of tumor necrosis factor alpha (TNFα), interleukin 1 beta (IL-1β), polyinosinic:polycytidylic acid (referred to herein as poly-I:C, pI:C or p-IC), granulocyte-macrophage colony-stimulating factor (GM-CSF), lipopolysaccharide (LPS), or combinations thereof.

Exposure of an immature DC cell or cell population to one or more of TNFα, IL-1β, poly-I:C, GM-CSF, and LPS can be performed prior to, subsequent to, or concurrent with exposure to type 1 interferon and type 2 interferon. Alternatively, the exposure of an immature DC cell or cell population to one or more of TNFα, IL-1β, poly-I:C, GM-CSF, and LPS can be performed between exposure to type 1 interferon and type 2 interferon, wherein the type 1 interferon and type 2 interferon are exposed to the immature DC cell or cell population in any order. In some embodiments, the immature DC is exposed to one or more of TNFα, IL-1β, poly-I:C, GM-CSF and LPS before exposure to the one or more of a type 1 interferon and one or more of a type 2 interferon. In some embodiments, multiple (e.g., two or more) exposures to any exposure agent (e.g., type 1 interferon, type 2 interferon, TNFα, IL-1β, poly-I:C, GM-CSF, LPS, etc.) can be used, and the timing of any given exposure can vary in relation to exposures to the same or other exposure agents (e.g., one or more of TNFα, IL-1β, poly-I:C, GM-CSF, and LPS can be exposed to an immature DC cell or cell population both before and after the immature DC cell or cell population is exposed to type 1 interferon and type 2 interferon).

In some embodiments, exposure of an immature DC cell or cell population to one or more of TNFα, IL-1β, poly-I:C, GM-CSF, and LPS can be performed immediately prior to or subsequent to exposure to one or more type 1 interferon and one or more type 2 interferon. In some embodiments, exposure of an immature DC cell or cell population to one or more of TNFα, IL-1β, poly-I:C, GM-CSF, and LPS can be performed within 15 minutes, 30 minutes, or 45 minutes of exposure to one or more type 1 interferon and one or more type 2 interferon. In some embodiments, exposure of an immature DC cell or cell population to one or more of TNFα, IL-1β, poly-I:C, GM-CSF, and LPS can be performed within 1 hour, 2 hours, 3 hours, 5 hours, 10 hours, 12 hours, or 18 hours of exposure to one or more type 1 interferon and one or more type 2 interferon. In some embodiments, exposure of an immature DC cell or cell population to one or more of TNFα, IL-1β, poly-I:C, GM-CSF, and LPS can be performed within 1 day, 2 days, 3 days, or 5 days or more of exposure to one or more type 1 interferon and one or more type 2 interferon.

The amount of exposure agent used to expose to an immature DC cell or cell population (e.g., type 1 interferon, type 2 interferon, TNFα, IL-1β, poly-I:C, GM-CSF, LPS, etc.) can vary based on the agent used, the nature of the immature DC cell or cell population. However, the amount used should be an amount sufficient to result in a ST-αDC1 phenotype, the exact amounts being determinable by those of skill in the art. In some embodiments, the immature DC cell or cell population is exposed to IFNα in an amount ranging from 1 U/mL to 10,000,000 U/mL, from 10 U/mL to 1,000,000 U/mL, from 100 U/mL to 100,000 U/mL, from 100 U/mL to 10,000 U/mL, or in an amount of about 1000 U/ml. In some embodiments, the immature DC cell or cell population is exposed to IFNγ in an amount ranging from 1 U/mL to 10,000,000 U/mL, from 10 U/mL to 1,000,000 U/mL, from 100 U/mL to 100,000 U/mL, from 100 U/mL to 10,000 U/mL, or in an amount of about 500 U/ml. In some embodiments, the immature DC cell or cell population is exposed to p-IC in an amount ranging from 10 pg/mL to 100 mg/mL, from 1 ng/mL to 10 mg/mL, from 10 ng/mL to 1 mg/mL, from 1 μg/mL to 100 μg/mL, or in an amount of about 10 μg/ml. In some embodiments, the immature DC cell or cell population is exposed to TNFα in an amount ranging from 10 pg/mL to 100 mg/mL, from 100 pg/mL to 1 mg/mL, from 1 ng/mL to 10 μg/mL, from 1 ng/mL to 100 ng/mL, or in an amount of about 5 ng/ml. In some embodiments, the immature DC cell or cell population is exposed to IL1β in an amount ranging from 10 pg/mL to 100 mg/mL, from 100 pg/mL to 1 mg/mL, from 1 ng/mL to 10 μg/mL, from 1 ng/mL to 100 ng/mL, or in an amount of about 25 ng/μl. In some embodiments, the immature DC cell or cell population is exposed to GM-CSF in an amount ranging from 1 U/mL to 10,000,000 U/mL, from 10 U/mL to 1,000,000 U/mL, from 100 U/mL to 100,000 U/mL, from 100 U/mL to 10,000 U/mL, or in an amount of about 1000 U/ml.

The ST-αDC1 phenotype includes, for example, production of increased levels of IL-12, CCL5, CXCL9, and/or CXCL10. In some embodiments, levels of IL-12, CCL5, CXCL9, and/or CXCL10 in a ST-αDC1 phenotype are increased by at least 10%, at least 25%, at least 50%, at least 75%, at least 100%, at least 150% (i.e. 1.5-fold), at least 200% (i.e. 2-fold), at least 300% (i.e. 3-fold), or at least 500% (i.e. 5-fold) compared to a control (e.g., αDC1 cells which are not short-term activated, are short term activated in the absence of type-1 and type-2 IFNs, using IL-1β and TNFα, TNFα alone, poly-I:C, LPS, or another TLR ligand, and/or are activated for 24 hours or more).

A ST-αDC1, in some embodiments, can be characterized as having high expression of co-stimulatory factors and/or CTL-attractants, and are not exhausted. In some embodiments, a ST-αDC1 produces increased levels of IL-12, CCL5, CXCL9, and/or CXCL10 for at least 4 hours, at least 8 hours, at least 12 hours, or at least 24 hours. In some embodiments, a ST-αDC1 produces increased levels of IL-12, CCL5, CXCL9, and/or CXCL10 for at least 2 days, at least 3 days, or at least 5 days. Duration of increased expression of IL-12, CCL5, CXCL9, and/or CXCL10 can be measured in vitro (e.g., in a cell culture) or in vivo.

In some embodiments, the one or more ST-αDC1 cell or cell population results from exposure of an immature DC cell or cell population to one or more type 1 interferon and one or more type 2 interferon for a defined period of time. In some embodiments, the exposure of an immature DC cell or cell population to one or more type 1 interferon and one or more type 2 interferon is for a time less than (e.g., less than 24 hours) the time required to achieve complete maturation of the DC cell or cell population. In some embodiments, the exposure of an immature DC cell or cell population to one or more type 1 interferon and one or more type 2 interferon is for less than 16 hours. In some embodiments, the exposure of an immature DC cell or cell population to one or more type 1 interferon and one or more type 2 interferon is for less than 12 hours, less than 8 hours, or less than 4 hours. In some or further embodiments, the exposure of an immature DC cell or cell population to one or more type 1 interferon and one or more type 2 interferon is for between 1 hour and 12 hours, between 1 hour and 8 hours, or between 1 hour and 4 hours. In some or further embodiments, the exposure of an immature DC cell or cell population to one or more type 1 interferon and one or more type 2 interferon is for between 2 hours and 12 hours, between 2 hours and 8 hours, or between 2 hours and 4 hours. In some or further embodiments, the exposure of an immature DC cell or cell population to one or more type 1 interferon and one or more type 2 interferon is for between 3 hours and 12 hours, between 3 hours and 8 hours, or between 3 hours and 4 hours. In some embodiments, the exposure of an immature DC cell or cell population to one or more type 1 interferon and one or more type 2 interferon is for approximately 1 hour, 2 hours, 3 hours, or 4 hours.

In some embodiments, the methods increase induction immunity, effector immunity, or combinations thereof. In some embodiments, the ST-αDC1s can produce increased levels of chemokines which attract cytotoxic T-lymphocyte (CTL), Type-1 T-helper (Th1), and natural killer (NK) cells. In some embodiments, the ST-αDC1s can produce increased levels of such attractant chemokines even in the presence of suppressive tumor microenvironments (TME). In some embodiments, the CTL-, Th1-, and/or NK cell-attractant chemokines comprise C-C Motif Chemokine Ligand 5 (CCL5), C-X-C Motif Chemokine Ligand 9 (CXCL9), C-X-C Motif Chemokine Ligand 10 (CXCL10), Interleukin 12 (IL-12), or any combination thereof.

Levels of a CTL-, Th1-, and/or NK cell-attractant chemokine can be determined via a wide array of methods used to determine polynucleotide levels, polypeptide levels, or combinations thereof. As used herein, the "level" of a polynucleotide or polypeptide refers to an expression level (e.g., an amount of detectable polynucleotide or polypeptide).

For example, a level of a CTL-, Th1-, and/or NK cell-attractant chemokine can be determined as a level of polypeptide expression, which refers to a qualitative or quantitative amount of polypeptide within the sample or control, for example, the amount produced by the cells in the sample or control. Polypeptide expression levels can be determined by a number of methods, including radiation absorbance (e.g., ultraviolet light absorption at 260, 280, or 230 nm), bicinchoninic acid (BCA) assay, Bradford assay, biuret test, Lowry method, Coomassie-blue staining, silver-staining, immunodetection and/or Western blot analysis, and other suitable methods.

Alternatively, or in addition to, a level of a CTL-, Th1-, and/or NK cell-attractant chemokine can be determined as a level of polynucleotide expression, which refers to a qualitative or quantitative amount of RNA polynucleotide within the sample or control, for example, within the cells of the sample or control. Polynucleotide expression levels such as mRNA transcript levels can be determined by a number of methods, including radiation absorbance (e.g., ultraviolet light absorption at 260, 280, or 230 nm), quantification of fluorescent dye or tag emission (e.g., ethidium bromide intercalation), quantitative polymerase chain reaction (qPCR) of cDNA produced from mRNA transcripts, southern blot analysis, gene expression microarray, or other suitable methods. Levels of mRNA transcripts can also be used to infer or estimate levels of polypeptide expression.

The determined level of a CTL-, Th1-, and/or NK cell-attractant chemokine can be compared to a control. In some embodiments, the level of a CTL-, Th1-, and/or NK cell-attractant chemokine is at least 50% increased compared to a control. In some embodiments, the level of a CTL-, Th1-, and/or NK cell-attractant chemokine is at least 75%, at least 90%, or at least 95% increased compared to a control. In some embodiments, the level of a CTL-, Th1-, and/or NK cell-attractant chemokine is at least two-fold, at least three-fold or at least five-fold increased compared to a control.

The control can comprise a biological sample, or alternatively, a collection of values used as a standard applied to one or more subjects (e.g., a general number or average that is known and not identified in the method using a sample). In some embodiments, the control can comprise one or more dendritic cells having a longer term exposure to a type 1 interferon and a type 2 interferon, for example an exposure for at least 24 hours, at least 36 hours, or at least 48 hours. In some embodiments, the control is an untreated dendritic cell. In some or further embodiments, the control can comprise one or more dendritic cells of the subject.

The ST-αDC1s, or populations of ST-αDC1s, can be administered to the subject via various methods. Using any one or more of the various routes of administration, the ST-αDC1 cells or cell populations can, in some embodiments, be administered systemically. "Systemic administration" refers to the introducing or delivering to a subject an agent via a route which introduces or delivers the agent to extensive areas of the subject's body (e.g. greater than 50% of the body), for example through entrance into the circulatory or lymph systems. Alternatively, the ST-αDC1 cells or cell populations can, in some embodiments, be administered locally. "Local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration by any route includes self-administration and the administration by another. In some embodiments, the administration is intratumoral.

The amount of active agent (e.g., one or more ST-αDC1 cells or cell populations) administered to the subject can vary widely but should be sufficient to therapeutically treat the target condition (e.g., a cancer). The amount of active agent administered to the subject can be expressed in terms of a dosage amount per body weight. The amount of the disclosed active agent administered will vary from subject to subject, depending on the nature of the disclosed compositions and/or formulations, the species, gender, age, weight and general condition of the subject, the mode of administration, and the like. Effective dosages and schedules for administering the compositions may be determined empirically, and making such determinations is within the skill in the art. The dosage ranges for the administration of the disclosed compositions are those large enough to produce the desired effect (e.g., to reduce tumor growth). The dosage should not be so large as to outweigh benefits by causing adverse side effects, such as unwanted cross-reactions, anaphylactic reactions, and the like. The dosage can be adjusted by the individual clinician in the event of any counterindications. Generally, the disclosed compositions and/or formulations are administered to the subject at a dosage of active component(s) ranging from 0.1 µg/kg body weight to 100 g/kg body weight. In some embodiments, the disclosed compositions and/or formulations are administered to the subject at a dosage of active component(s) ranging from 1 µg/kg to 10 g/kg, from 10 µg/kg to 1 g/kg, from 10 µg/kg to 500 mg/kg, from 10 µg/kg to 100 mg/kg, from 10 µg/kg to 10 mg/kg, from 10 µg/kg to 1 mg/kg, from 10 µg/kg to 500 µg/kg, or from 10 µg/kg to 100 µg/kg body weight. Dosages above or below the range cited above may be administered to the individual subject if desired.

The methods can comprise one or more dosages of an agent (e.g., one or more ST-αDC1 cells or cell populations), for example, at least one, at least two, at least three, at least four, at least five, at least six, at least seven, at least eight, at least nine, or at least ten dosages. Administration of the dosages can be performed before the subject exhibits symptoms of a disease or disorder (e.g., prophylactically), or during or after symptoms of a disease occur.

In some embodiments, a subsequent administration of a dose is provided at least one day after a prior administration of a dose, or at least two days, at least three days, at least four days, at least five days, or at least six days after a prior administration of a dose. In some embodiments, a subsequent administration is provided at least one week after a prior administration, or at least two weeks, at least three weeks, or at least four weeks after a prior administration of a dose. In some embodiments, a subsequent administration is provided at least one month, at least two months, or at least three months after a prior administration. Further provided herein are methods of using the ST-αDC1s for the treatment of a precancerous condition or chronic infection. The term "precancerous condition" includes any condition which may develop into a cancer, including chronic infections (including, but not limited to, those mediated by HIV, HPV, Hepatitis B, Hepatitis C, EBV, CMV, M. tuberculosis, and intracellular bacteria and parasites), as well as chronic inflammatory states, including inflammatory bowel disease (including Crohn's and ulcerative colitis), Barrett's esophagus, Ductal carcinoma in situ (CIS), cervical intraepithelial neoplasia (CIN), vulvar intraepithelial neoplasia (VIN), chronic pancreatitis, chronic hepatitis (viral and non-viral etiologies), lymphoproliferative syndromes, chronic gastritis, chronic esophagitis, chronic obstructive pulmonary disease (COPD) and globulinopathies. Accordingly, provided herein is a method of treating a precancerous condition or chronic infection in a subject comprising administering to the subject a pharmaceutically effective amount of an ST-αDC1 composition as described herein.

Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer or precancerous condition including, but not limited to, a chronic infection. Prophylactic administration can occur for several days to years prior to the manifestation of symptoms of cancer. In some instances, the terms "treat," "treating," "treatment" and grammatical variations thereof, include partially or completely reducing the size of a tumor, reducing the number of tumors, and reducing the spread or incidence of a cancer as compared with prior to treatment of the subject or as compared with the incidence of such symptom in a general or study population. Accordingly, the methods of treatment may comprise adoptive cell therapies (ACT) or vaccination therapies.

The methods can be performed with or without administration of additional agents (e.g., therapeutic agents, diagnostic agents). In some embodiments, the methods can include administering one or more additional anti-cancer therapeutics in addition to administering the disclosed compositions or agents. It is understood that the methods can encompass any known anti-cancer therapeutic, the specific class of which are not particularly limited. Non-limiting examples of suitable anti-cancer therapeutics which can be used in the methods include Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride) and other DNA intercalators, Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), altretamine, Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, antiangiogenic agents such as angiostatin, antiestrogens such as tamoxifen, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical) and other antimetabolites, Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide and other topoisomerase inhibitors (e.g., camptothecin), Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide and other alkylating agents, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Margibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel) and other mitotic inhibitors, Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate), busulphan, calcium folinate, vindesine, crisantaspase, gefitinib (IRESSA), hydroxyurea, pentostatin, raltitrexed, streptozocin, tegafur-uracil, tioguanine/thioguanine, treosulfan, vinorelbine, and combinations thereof.

In some embodiments, the methods further comprise administering a checkpoint inhibitor. Checkpoint inhibitors (sometimes referred to as checkpoint blockade inhibitors (CBI) or checkpoint blockades) can increase the effectiveness of overall T cell anti-tumor or anti-cancer immunity. Checkpoint inhibitors can inhibit certain activities of particular proteins produced by immune cells (e.g., T cells) and cancer cells that keep immune cells "in check," or in other words, prevent immune cells from attacking or killing a cell (e.g., cancer cell). When a checkpoint inhibitor inhibits checkpoint proteins, immune cells such as T cells can more effectively mount a response to the cancer cell.

The checkpoint inhibitor can comprise a programmed death protein 1 (PD-1) inhibitor, a programmed death protein ligand 1 or 2 (PDL1 or PDL2) inhibitor, a cytotoxic T-lymphocyte-associated protein 4 (CTLA-4) inhibitor, Lymphocyte-activation gene 3 (LAG3) inhibitor, T-cell Immunoglobulin domain and Mucin domain 3 (TIM-3) inhibitor, V-domain Ig suppressor of T cell activation (VISTA) inhibitor, B and T Lymphocyte Attenuator (BTLA) inhibitor, or combinations thereof. In some embodiments, the checkpoint inhibitor comprises an antibody (e.g., a monoclonal antibody) against PD-1, PDL1, PDL2, or CTLA-4. An anti-PD-1 antibody, an anti-PDL1 antibody, and an anti-CTLA4 antibody are defined herein as a polypeptide capable of specifically binding to PD-1, PDL1, and CTLA4 polypeptides, respectively.

Suitable examples of PD-1 inhibitors include, but are not limited to, nivolumab (Bristol-Myers Squibb), pembrolizumab (Merck), pidilizumab (CureTech/Teva), AMP-244 (Amplimmune/GSK), BMS-936559 (BMS), and MEDI4736 (Roche/Genentech), or any combination thereof. Suitable examples of PDL1 inhibitors include, but are not limited to, atezolizumab, durvalumab (AstraZeneca), avelumab, or any combination thereof. Suitable examples of CTLA4 inhibitors include, but are not limited to, abatacept, belatacept, ipilimumab, tremelimumab, or any combination thereof.

The ST-αDC1s administered to a subject can be formulated with a pharmaceutically acceptable carrier and/or as a medicament. Suitable carriers include, but are not limited to, salts, diluents, binders, fillers, solubilizers, disintegrants, preservatives, sorbents, and other components.

Methods of Making ST-αDC1s

Provided herein are ST-αDC1s that have been created through exposure to a combination of one or more of a type 1 interferon (i.e., IFNα, IFNβ, IFN-κ, IFNω and IFNν) and one or more of a type 2 interferon (IFNγ) for less than 16 hours.

ST-αDC1 cells can be obtained from manipulations (e.g., exposure to activating agents, immunomodulators, etc.) performed on immature DC cells. The immature DC cell can be any DC capable of conversion to a ST-αDC1 cell, and thus typically requires that the DC cell be fully immature or partially immature (e.g., the DC cell is not completely mature). The immature DC cell can be obtained from a stock cell bank, but is typically obtained from the subject. Alternatively, the immature DC cell can be a cell which results from reprogramming a stem cell (e.g., a tissue stem cell or an induced pluripotent stem cell) of the subject to express an immature DC cell phenotype.

Suitable type 1 interferons include IFNα, IFNβ, IFN-κ, IFNω and IFNν. In non-human animals, type 1 interferons can also include IFNε, IFNτ, IFNδ, and IFNζ. Suitable type 2 interferons include IFNγ. In non-human animals, type 2 interferons can also include IFNγ1 and IFNγ2.

Exposure of an immature DC cell or cell population to a type 1 interferon can be performed prior to, subsequent to, or concurrent with exposure to a type 2 interferon. In some embodiments, the immature DC cell or cell population is exposed to one or more type 1 interferon and one or more type 2 interferon for substantially the same time period.

In some embodiments, the methods can include exposing an immature DC cell or cell population to one or more of TNFα, IL-1β, poly-I:C, GM-CSF, LPS, or combinations thereof.

Exposure of an immature DC cell or cell population to one or more of TNFα, IL-1β, poly-I:C, GM-CSF, and LPS can be performed prior to, subsequent to, or concurrent with exposure to type 1 interferon and type 2 interferon. Alternatively, the exposure of an immature DC cell or cell population to one or more of TNFα, IL-1β, poly-I:C, GM-CSF, and LPS can be performed between exposure to type 1 interferon and type 2 interferon, wherein the type 1 interferon and type 2 interferon are exposed to the immature DC cell or cell population in any order. In some embodiments, the immature DC is exposed to one or more of TNFα, IL-1β, poly-I:C, GM-CSF and LPS before exposure to the one or more of a type 1 interferon and one or more of a type 2 interferon. In some embodiments, multiple (e.g., two or more) exposures to any exposure agent (e.g., type 1 interferon, type 2 interferon, TNFα, IL-1β, poly-I:C, GM-CSF, LPS, etc.) can be used, and the timing of any given exposure can vary in relation to exposures to the same or other exposure agents (e.g., one or more of TNFα, IL-1β, poly-I:C, GM-CSF, and LPS can be exposed to an immature DC cell or cell population both before and after the immature DC cell or cell population is exposed to type 1 interferon and type 2 interferon).

In some embodiments, exposure of an immature DC cell or cell population to one or more of TNFα, IL-1β, poly-I:C, GM-CSF, and LPS can be performed immediately prior to or subsequent to exposure to one or more type 1 interferon and one or more type 2 interferon. In some embodiments, exposure of an immature DC cell or cell population to one or more of TNFα, IL-1β, poly-I:C, GM-CSF, and LPS can be performed within 15 minutes, 30 minutes, 45 minutes, 1 hour, 2 hours, 3 hours, 5 hours, 10 hours, 12 hours, 18 hours, 1 day, 2 days, 3 days, or 5 days or more of exposure to one or more type 1 interferon and one or more type 2 interferon.

The amount of exposure agent used to expose to an immature DC cell or cell population (e.g., type 1 interferon, type 2 interferon, TNFα, IL-1B, poly-I:C, GM-CSF, LPS, etc.) can vary based on the agent used, the nature of the immature DC cell or cell population. However, the amount used should be an amount sufficient to result in a ST-αDC1 phenotype, the exact amounts being determinable by those of skill in the art.

In some embodiments, the immature DC cell or cell population is exposed to IFNα in an amount ranging from 1 U/mL to 10,000,000 U/mL, from 10 U/mL to 1,000,000 U/mL, from 100 U/mL to 100,000 U/mL, from 100 U/mL to 10,000 U/mL, or in an amount of about 1000 U/ml. In some embodiments, the immature DC cell or cell population is exposed to IFNγ in an amount ranging from 1 U/mL to 10,000,000 U/mL, from 10 U/mL to 1,000,000 U/mL, from 100 U/mL to 100,000 U/mL, from 100 U/mL to 10,000 U/mL, or in an amount of about 500 U/ml. In some embodiments, the immature DC cell or cell population is exposed to p-IC in an amount ranging from 10 pg/mL to 100 mg/mL, from 1 ng/mL to 10 mg/mL, from 10 ng/mL to 1 mg/mL, from 1 μg/mL to 100 μg/mL, or in an amount of about 10 μg/ml. In some embodiments, the immature DC cell or cell population is exposed to TNFα in an amount ranging from 10 pg/mL to 100 mg/mL, from 100 pg/mL to 1 mg/mL, from 1 ng/mL to 10 μg/mL, from 1 ng/mL to 100 ng/mL, or in an amount of about 5 ng/ml. In some embodiments, the immature DC cell or cell population is exposed to IL1β in an amount ranging from 10 pg/mL to 100 mg/mL, from 100 pg/mL to 1 mg/mL, from 1 ng/mL to 10 μg/mL, from 1 ng/mL to 100 ng/mL, or in an amount of about 25 ng/μl. In some embodiments, the immature DC cell or cell population is exposed to GM-CSF in an amount ranging from 1 U/mL to 10,000,000 U/mL, from 10 U/mL to 1,000,000 U/mL, from 100 U/mL to 100,000 U/mL, from 100 U/mL to 10,000 U/mL, or in an amount of about 1000 U/ml.

The ST-αDC1 phenotype includes, for example, production of increased levels of IL-12, CCL5, CXCL9, and/or CXCL10. In some embodiments, levels of IL-12, CCL5, CXCL9, and/or CXCL10 in a ST-αDC1 phenotype are increased by at least 10%, at least 25%, at least 50%, at least 75%, at least 100%, at least 150% (i.e. 1.5-fold), at least 200% (i.e. 2-fold), at least 300% (i.e. 3-fold), or at least 500% (i.e. 5-fold) compared to a control (e.g., αDC1 cells which are not short-term activated, are short term activated using IL-1β and TNFα or LPS, or poly-I:C, and/or are activated for 24 hours or more).

In some embodiments, a ST-αDC1 produces increased levels of IL-12, CCL5, CXCL9, and/or CXCL10 for at least 4 hours, at least 8 hours, at least 12 hours, or at least 24 hours. In some embodiments, a ST-αDC1 produces increased levels of IL-12, CCL5, CXCL9, and/or CXCL10 for at least 2 days, at least 3 days, or at least 5 days.

In some embodiments, the one or more ST-αDC1 cell or cell population results from exposure of an immature DC cell or cell population to one or more type 1 interferon and one or more type 2 interferon for a defined period of time. In some embodiments, the exposure of an immature DC cell or cell population to one or more type 1 interferon and one or more type 2 interferon is for a time less than (e.g., less than 24 hours) the time required to achieve complete maturation of the DC cell or cell population. In some embodiments, the exposure of an immature DC cell or cell population to one or more type 1 interferon and one or more type 2 interferon is for less than 16 hours, less than 12 hours, less than 8 hours, or less than 4 hours. In some or further embodiments, the exposure of an immature DC cell or cell population to one or more type 1 interferon and one or more type 2 interferon is for between 1 hour and 12 hours, between 1 hour and 8 hours, between 1 hour and 4 hours, between 2 hours and 12 hours, between 2 hours and 8 hours, between 2 hours and 4 hours, between 3 hours and 12 hours, between 3 hours and 8 hours, or between 3 hours and 4 hours. In some embodiments, the exposure of an immature DC cell or cell population to one or more type 1 interferon and one or more type 2 interferon is for approximately 1 hour, 2 hours, 3 hours, or 4 hours.

In some embodiments, the methods increase induction immunity, effector immunity, or combinations thereof. In some embodiments, the ST-αDC1s can produce increased levels of chemokines which attract cytotoxic T-lymphocyte (CTL), Type-1 T-helper (Th1), and natural killer (NK) cells. In some embodiments, the ST-αDC1s can produce increased levels of such attractant chemokines even in the presence of suppressive tumor microenvironments (TME). In some embodiments, the CTL-, Th1-, and/or NK cell-attractant chemokines comprise CCL5, CXCL9, CXCL10, IL-12, or any combination thereof.

Levels of a CTL-, Th1-, and/or NK cell-attractant chemokine can be determined via a wide array of methods used to determine polynucleotide levels, polypeptide levels, or combinations thereof. For example, a level of a CTL-, Th1-, and/or NK cell-attractant chemokine can be determined as a level of polypeptide expression, which refers to a qualitative or quantitative amount of polypeptide within the sample or control, for example, within the cells of the sample or control. Alternatively, or in addition to, a level of a CTL-, Th1-, and/or NK cell-attractant chemokine can be determined as a level of polynucleotide expression, which refers to a qualitative or quantitative amount of RNA polynucleotide within the sample or control, for example, within the cells of the sample or control.

The determined level of a CTL-, Th1-, and/or NK cell-attractant chemokine can be compared to a control. In some embodiments, the increased production of IL-12, CCL5, CXCL9, and/or CXCL10 by the ST-αDC1 is at least about 5% higher, at least about 10% higher, at least about 25% higher, at least about 50% higher, at least about 75% higher, at least about 100% higher, at least about 150% (i.e. 1.5-fold) higher, at least about 200% (i.e. 2-fold) higher, at least about 300% (i.e. 3-fold) higher, or at least about 500% (i.e. 5-fold) higher than a control (e.g., αDC1 cells which are not short-term activated, are short term activated using IL-1β and TNFα TNFα alone or LPS, poly-I:C or other TLR ligand, but in the absence of type-1 and type-2 IFNs, and/or are activated for 24 hours or more). The term "higher" as used herein refers to either the percentage of IL-12, CCL5, CXCL9, and/or CXCL10 producing dendritic cells or the mean level of IL-12, CCL5, CXCL9, and/or CXCL10 production the population of cells, or both.

The control can comprise a biological sample, or alternatively, a collection of values used as a standard applied to one or more subjects (e.g., a general number or average that is known and not identified in the method using a sample). In some embodiments, the control can comprise one or more dendritic cells having a longer term exposure to a type 1 interferon and a type 2 interferon, for example an exposure for at least 24 hours, at least 36 hours, or at least 48 hours. In some embodiments, control dendritic cells/cell populations are those cells/cell populations that have been exposed to one or more of a type 1 interferon, a type 2 interferon, TNFα, poly-I:C, LPS, and GM-CSF for approximately 24 hours. Increased production of such CTL, Th1, and NK cell-attracting chemokines may be determined and/or measured via any method known to one of ordinary skill in the art. In some or further embodiments, the control can comprise one or more dendritic cells of the subject.

Also disclosed herein are ST-αDC1s made by the herein disclosed methods. For example, disclosed herein are ST-αDC1 cells made by exposing one or more immature DC cells to one or more of a type 1 interferon and one or more of a type 2 interferon for less than 16 hours, wherein the ST-αDC1 cell produces IL-12, CCL5, CXCL9, and/or CXCL10 at a level at least about 5% higher, at least about 10% higher, at least about 25% higher, at least about 50% higher, at least about 75% higher, at least about 100% higher, at least about 150% (i.e. 1.5-fold) higher, at least about 200% (i.e. 2-fold) higher, at least about 300% (i.e. 3-fold) higher, or at least about 500% (i.e. 5-fold) higher than a control (e.g., αDC1 cells which are not short-term activated, are short term activated using IL-1β and TNFα, TNFα, poly-I:C, LPS, or other TLR ligand, and/or are activated for 24 hours or more). In some embodiments, the ST-αDC1 cell is made by exposing one or more immature DC cells to one or more of a type 1 interferon and one or more of a type 2 interferon for less than 16 hours, wherein the ST-αDC1 cell produces at least 50% increased CXCL10 compared to a αDC1 cell activated for 24 hours or more. In some embodiments, the ST-αDC1 cell made by any herein disclosed method produces at least 50% increased CXCL10 compared to a short-term activated dendritic cell which is activated for less than 24 hours by addition of IL-1β and TNFα, TNFα, poly-I:C, LPS, or other TLR ligand, but in the absence of type-1 and type-2 IFNs.

As the ST-αDC1s and/or ST-αDC1 populations can be used for the treatment of cancer, precancerous condition or chronic infection, also included herein are medicaments and pharmaceutical compositions comprising the ST-αDC1s and/or ST-αDC1 populations. The medicaments and pharmaceutical compositions comprise pharmaceutically effective amounts of the ST-αDC1s and/or ST-αDC1 populations. Further included herein are ST-αDC1s and/or ST-αDC1 populations created using the methods described herein.

Also provided herein are methods of making ST-αDC1s that comprise the steps of 1) providing one or more immature DC cells, and 2) exposing the cells to one or more of a type 1 interferon and one or more of a type 2 interferon for less than 16 hours. In some embodiments the exposure is less than or approximately 12 hours, less than or approximately 8 hours, or less than or approximately 4 hours. In some embodiments, the type 1 interferon is IFNα.

In other embodiments, the method further comprises exposure of the immature DC cell to one or more of TNFα, poly-I:C, LPS, IL-1β, and GM-CSF. The immature DC cell can be exposed to the TNFα, poly-I:C, LPS and/or IL-1β prior to or after the exposure to the one or more of a type 1 interferon and one or more of a type 2 interferon. In some embodiments the exposure to the TNFα, poly-I:C, LPS and/or IL-1β is prior to the exposure to the one or more of a type 1 interferon and one or more of a type 2 interferon.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

I claim:
1. A method of making an ST-αDC1 cell or cell population in vitro comprising, exposing one or more immature DC cells to IFNα, IFNγ, TNFα, poly-I:C, and IL-1β for about 4 hours or less and removing the IFNα, IFNγ, TNFα, poly-I:C, and IL-1β at about 4 hours or less, and wherein the ST-αDC1 cell or cell population produces IL-12p70 in an amount increased at least 100% as compared to a control, wherein the control is an immature DC cell that is exposed for about 24 hours to IFNα, IFNγ, TNFα, poly-I:C, and IL-1β.

2. The method of claim 1, further comprising exposing the one or more immature DC cells to LPS.

3. The method of claim 2, wherein the one or more immature DC cells are exposed to the TNFα, poly-I:C, and IL-1β to create a first mixture, the IFNα and IFNγ are later added to the first mixture, and all of the IFNα, IFNγ, TNFα, poly-I:C, and IL-1β are removed at about 4 hours or less from the creation of the first mixture.

4. The method of claim 1, wherein the ST-αDC1 cell or cell population produces IL-12p70 in an amount increased at least 150% as compared to the control.

5. The method of claim 1, wherein the wherein the ST-αDC1 cell or cell population produces IL-12p70 in an amount increased at least 200% as compared to the control.

* * * * *

UNITED STATES PATENT AND TRADEMARK OFFICE
CERTIFICATE OF CORRECTION

PATENT NO. : 12,059,434 B2
APPLICATION NO. : 16/488702
DATED : August 13, 2024
INVENTOR(S) : Pawel Kalinski Page 1 of 1

It is certified that error appears in the above-identified patent and that said Letters Patent is hereby corrected as shown below:

In the Specification

In Column 6, Line 26, "intrastemal" should be changed to -- intrasternal --.
In Column 19, Line 49, "Margibo" should be changed to -- Marqibo --.

In the Claims

In Claim 1, Column 26, Line 25 (Approx.), "poly-LC" should be changed to -- poly-I:C --.
In Claim 5, Column 26, Line 44 (Approx.), "wherein the wherein the" should be changed to -- wherein the --.

Signed and Sealed this
Eleventh Day of February, 2025

Coke Morgan Stewart
*Acting Director of the United States Patent and Trademark Office*